(12) United States Patent
Shin et al.

(10) Patent No.: US 9,259,481 B2
(45) Date of Patent: Feb. 16, 2016

(54) DEVELOPMENT OF NOVEL MACROMOLECULE TRANSDUCTION DOMAIN WITH IMPROVED CELL PERMEABILITY AND METHOD FOR USING SAME

(71) Applicant: Procell Therapeutics Inc., Seoul (KR)

(72) Inventors: Ki Deok Shin, Daejeon (KR); Kang Jin Lee, Seoul (KR); Sunny Lim, Gyeonggi-do (KR); Byung Kyu Lee, Gyeonggi-do (KE); Jong Rae Kim, Seoul (KR)

(73) Assignee: Procell Therapeutics Inc., Seoul (KR)

( * ) Notice: Subject to any disclaimer, the term of this patent is extended or adjusted under 35 U.S.C. 154(b) by 0 days.

(21) Appl. No.: 14/360,317

(22) PCT Filed: Nov. 23, 2012

(86) PCT No.: PCT/KR2012/009997
§ 371 (c)(1),
(2) Date: May 23, 2014

(87) PCT Pub. No.: WO2013/077680
PCT Pub. Date: May 30, 2013

(65) Prior Publication Data
US 2014/0329737 A1 Nov. 6, 2014

Related U.S. Application Data

(60) Provisional application No. 61/563,110, filed on Nov. 23, 2011.

(51) Int. Cl.

| | | |
|---|---|---|
| A61K 38/08 | (2006.01) |
| A61K 38/10 | (2006.01) |
| C07K 7/08 | (2006.01) |
| C07K 7/06 | (2006.01) |
| A61K 47/48 | (2006.01) |
| A61K 8/64 | (2006.01) |
| A61Q 19/08 | (2006.01) |
| C12N 15/113 | (2010.01) |
| A61K 8/365 | (2006.01) |
| A61K 38/00 | (2006.01) |

(52) U.S. Cl.
CPC ........... *A61K 47/48246* (2013.01); *A61K 8/365* (2013.01); *A61K 8/64* (2013.01); *A61Q 19/08* (2013.01); *C07K 7/06* (2013.01); *C07K 7/08* (2013.01); *C12N 15/113* (2013.01); *A61K 38/00* (2013.01); *C07K 2319/00* (2013.01); *C12N 2320/32* (2013.01)

(58) Field of Classification Search
CPC .. C12N 15/87; C12N 15/113; C12N 2320/32; A61K 38/00; A61K 8/64; A61K 47/48246; C07K 7/06; C07K 2319/00; C07K 7/08; A61Q 19/08
See application file for complete search history.

(56) References Cited

FOREIGN PATENT DOCUMENTS

| KR | 10-2009-7017564 | 8/2009 |
|---|---|---|
| KR | 10-116903 | 7/2012 |
| WO | 03/097671 | 11/2003 |
| WO | 2008/093982 | 8/2008 |
| WO | 2009/031835 A2 | 3/2009 |
| WO | 2009/031836 A1 | 3/2009 |

OTHER PUBLICATIONS

Green et al., "Autonomous functional domains of chemically synthesized human immunodeficiency virus tat trans-activator protein," *Cell*, 1998, 55(6):1179-88, Abstract only.
Frankel et al., "Cellular uptake of the tat protein from human immunodeficiency virus," *Cell*, 1988, 55(6):1189-93, Abstract only.
Vivès et al., "A Truncated HIV-1 Tat Protein Basic Domain Rapidly Translocates through the Plasma Membrane and Accumulates in the Cell Nucleus," *J. Biol. Chem.*, 1997, 272:16010-16017.
Futaki et al., "Arginine-rich Peptides: An Abundant Source of Membrane-Permeable Peptides having Potential as Carriers for Intracellular Protein Delivery," *J. Biol. Chem.*, 2001, 276:5836-5840.
Wadia et al., "Protein transduction technology," *Current Opinion in Biotechnology*, 2002, 13:52-56.
Wadia et al., "Transducible TAT-HA fusogenic peptide enhances escape of TAT-fusion proteins after lipid raft macropinocytosis," *Nature Medicine*, 2004, 10(3):310-315.
Joliot et al., "Antennapedia homeobox peptide regulates neural morphogenesis," *Proc. Natl. Acad. Sci. USA*, 1991, 88:1864-1868.
Derossi et al., "The Third Helix of the Antennapedia Homeodomain Translocates through Biological Membranes," *The Journal of Biological Chemistry*, 1994, 269(14):10444-10450.
Joliot et al., "Transduction peptides: from technology to physiology," *Nature Cell Biology*, 2004, 6(3):189-196.
Nakase et al., "Interaction of Arginine-Rich Peptides with Membrane-Associated Proteoglycans is Crucial for Induction of Actin Organization and Macropinocytosis," *Biochemistry*, 2007, 46:492-501.

(Continued)

*Primary Examiner* — Julie Ha
*Assistant Examiner* — Li Ni Komatsu
(74) *Attorney, Agent, or Firm* — Riverside Law LLP

(57) ABSTRACT

The present invention relates to an improved macromolecule transduction domain (MTD), which facilitates permeating the cell membrane of a biologically active molecule, having enhanced cell permeability. Specifically, an improved MTD according to the present invention, compared to an existing MTD, can transmit various types of biologically active molecule from inside the body and inside a test tube more effectively, and thus can be effectively used in a method to genetically alter a biologically active molecule so as to have cell permeability or in a method to transport a biologically active molecule into a cell, or the like. Additionally, the improved MTD can be very useful in development of new drugs and incrementally modified drugs as uses of the improved MTD are possible in drug delivery systems, recombinant protein vaccines or DNA/RNA therapeutic agents, gene or protein therapies, and pharmacologically or medically useful protein production or medical, pharmacological and pharmaceutical compositions.

4 Claims, 15 Drawing Sheets

(56) References Cited

OTHER PUBLICATIONS

Åmand et al., "Binding of cell-penetrating penetratin peptides to plasma membrane vesicles correlates directly with cellular uptake," *Biochimica et Biophysica Acta*, 2011, 1808:1860-1867.

Milletti, "Cell-penetrating peptides: classes, origin, and current landscape," *Drug Discovery Today*, 2012, 17(15/16):850-860.

Jo et al., "Epigenetic regulation of gene structure and function with a cell-permeable Cre recombinase," *Nature Biotechology*, 2001, 19:929-933.

Palva et al., "Secretion, of interferon by Bacillus subtilis," *Gene*, 1983, 22(2-3):229-35, Abstract only.

Mosbach et al., "Formation of proinsulin by immobilized Bacillus subtilis," *Nature*, 1983, 302(5908):543-5, Abstract only.

Frosch et al., "The soap chamber test. A new method for assessing the irritancy of soaps," *J. Am. Acad. Dermatol.*, 1979, 1(1):35-41, Abstract only.

Embury et al., "Proteins Linked to a Protein Transduction Domain Efficiently Transduce Pancreatic Islets," *Diabetes*, 2001, 50:1706-1713.

FIG. 1

| SEQ ID | | SEQUENCE | STRUCTURE |
|---|---|---|---|
| NO: 15 | MTD 1018 | Met Arg Ala Ala Leu Ile Gly Ala Val Leu Ala Pro Val Val Ala Val | 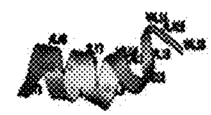 |
| NO: 22 | MTD 2018 | Met His Ala Ala Leu Ile Gly Ala Val Leu Ala Pro Val Val Ala Val | 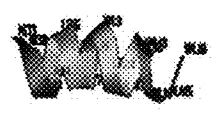 |
| NO: 29 | MTD 3018 | Met Lys Ala Ala Leu Ile Gly Ala Val Leu Ala Pro Val Val Ala Val | 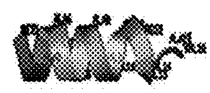 |
| NO: 16 | MTD 1067 | Met Arg Ala Ala Ala Pro Ala Val Ala Ala | 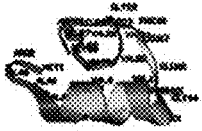 |
| NO: 23 | MTD 2067 | Met His Ala Ala Ala Pro Ala Val Ala Ala | 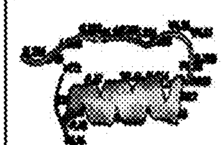 |
| NO: 30 | MTD 3067 | Met Lys Ala Ala Ala Pro Ala Val Ala Ala | 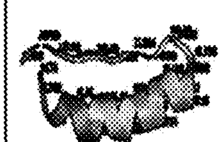 |
| NO: 17 | MTD 1103 | Met Arg Leu Ala Leu Pro Val Leu Leu Leu Ala | 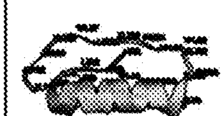 |

FIG. 2

| SEQ ID | | SEQUENCE | STRUCTURE |
|---|---|---|---|
| NO: 24 | MTD 2103 | Met His Leu Ala Leu Pro Val Leu Leu Leu Ala | 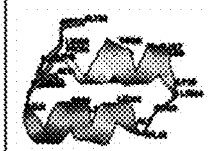 |
| NO: 31 | MTD 3103 | Met Lys Leu Ala Leu Pro Val Leu Leu Leu Ala | 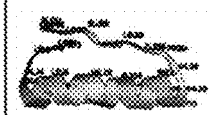 |
| NO: 18 | MTD 1159 | Met Arg Ile Ala Ile Ala Ala Ile Pro Ala Ile Leu Ala Leu | 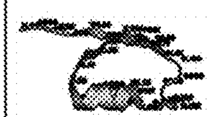 |
| NO: 25 | MTD 2159 | Met His Ile Ala Ile Ala Ala Ile Pro Ala Ile Leu Ala Leu | 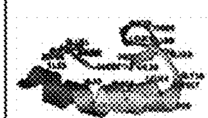 |
| NO: 32 | MTD 3159 | Met Lys Ile Ala Ile Ala Ala Ile Pro Ala Ile Leu Ala Leu | 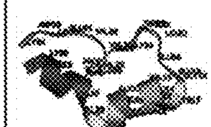 |
| NO: 19 | MTD 1173 | Met Arg Ala Val Ile Pro Ile Leu Ala Val Pro | 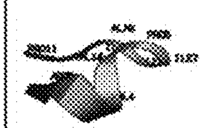 |
| NO: 26 | MTD 2173 | Met His Ala Val Ile Pro Ile Leu Ala Val Pro | 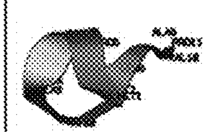 |

FIG. 3

| SEQ ID | | SEQUENCE | STRUCTURE |
|---|---|---|---|
| NO: 33 | MTD 3173 | Met Lys Ala Val Ile Pro Ile Leu Ala Val Pro | 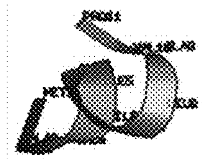 |
| NO: 6 | MTD 18m | Pro Ala Ala Leu Ala Ala Leu Pro Val Ala Val Val Ala Val | 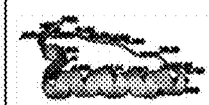 |
| NO: 20 | MTD 1018m | Met Arg Pro Ala Ala Leu Ala Ala Leu Pro Val Ala Val Val Ala Val | 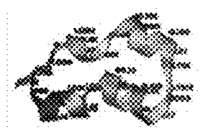 |
| NO: 27 | MTD 2018m | Met His Pro Ala Ala Leu Ala Ala Leu Pro Val Ala Val Val Ala Val | 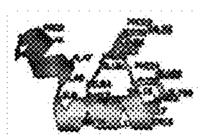 |
| NO: 34 | MTD 3018m | Met Lys Pro Ala Ala Leu Ala Ala Leu Pro Val Ala Val Val Ala Val | 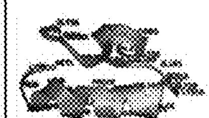 |
| NO: 7 | MTD 173A | Pro Ala Val Ile Pro Ile Leu Ala Val | 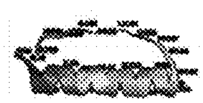 |
| NO: 21 | MTD 1173A | Met Arg Pro Ala Val Ile Pro Ile Leu Ala Val | 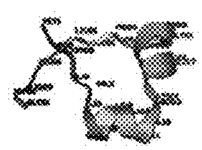 |

FIGURE
FIG. 4
| SEQ ID | | SEQUENCE | STRUCTURE |
|---|---|---|---|
| NO: 28 | MTD 2173A | Met His Pro Ala Val Ile Pro Ile Leu Ala Val | 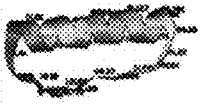 |
| NO: 35 | MTD 3173A | Met Lys Pro Ala Val Ile Pro Ile Leu Ala Val | 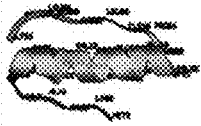 |

1. Lane: Invitrogen 10/60 Oligo length standard
2. Lane: Sulfo-4FB modified LacZ siRNA
3. Lane: LacZ siRNA conjugate with MTD2173A

DEVELOPMENT OF NOVEL MACROMOLECULE TRANSDUCTION DOMAIN WITH IMPROVED CELL PERMEABILITY AND METHOD FOR USING SAME

CROSS-REFERENCE TO RELATED APPLICATIONS

This application is the U.S. national phase application filed under 35 U.S.C. §371 claiming benefit to International Patent Application No. PCT/KR2012/009997, filed on Nov. 23, 2012, which is entitled to priority under 35 U.S.C. §119(e) to U.S. provisional application No. 61/563,110, filed Nov. 23, 2011, each of which application is hereby incorporated herein by reference in its entirety.

TECHNICAL FIELD

The present invention relates to a modified macromolecule transduction domain (MTD) having more improved cell permeability than a conventional MTD due to modification of an amino acid sequence of the conventional MTD, which facilitates delivery of a biologically active molecule to a cell, and a method of manufacturing the same, a polynucleotide encoding the modified MTD, a method of genetically engineering a biologically active molecule to have cell permeability using the modified MTD, and a method of importing a biologically active molecule into a cell using the modified MTD.

BACKGROUND ART

A cell membrane serves as an obstacle to permeability of proteins, nucleic acids, peptides and insoluble compounds into cells due to impermeability. This problem in intracellular drug transduction must be solved in fields of treatment, prevention and diagnosis of diseases. Generally, methods of permeating biologically active macromolecules into a cell membrane include electroporation, membrane fusion using a liposome, transfection using calcium phosphate, a cationic polymer such as polyethyleneimine (PEI) or DEAE-dextran, viral transfection, and single cell microinsertion. In addition, recently, for effective intracellular drug transduction, techniques of applying endocytosis of a drug delivery system such as nanoparticles have been used, but more studies on achieving effective intracellular drug delivery are needed due to a decrease in delivery efficiency caused by fast loss in an immune system, or steric hindrance caused by interaction with cells. Accordingly, recently, development of a method of delivering macromolecules such as proteins, nucleic acids, etc. through a biomembrane and a nuclear envelope of a cell without damage to a cell membrane has been continuously needed.

In 1988, the group of Green and Loewenstein (Green and Loewenstein. Cell 55, 1179-1188(188)) and the group of Frankel and Pabo (Frankel and Pabo. Cell 55, 1189-1193 (188)) each discovered a transduction domain permeating a transcription-associated protein, Tat, of HIV-1, which is the virus that causes acquired immune deficiency syndrome (AIDS), through a cell membrane and trans-activating a viral gene. A Tat domain exhibiting cell permeability is a sequence of 48th to 57th basic amino acids (GRKKRRQRRR; SEQ ID NO: 57) of the Tat protein, and it was found that the sequence serves an important role in permeating the cell membrane (Vives et al., J. Biol. Chem. 272, 16010-16017 (1997); Futaki et al, J. Biol. Chem. 276, 5836-5840 (2001); Wadia, J. S. and S. F. Dowdy, Cum Opin. Biotechnolol. 13(1): 52-6 (2002); Wadia et al, Nature Medicine 10(3), 310-315(2004)).

As another example, *Antennapedia homeodomain*-derived penetratin (RQIKIYFQNRRMKWKK; SEQ ID NO: 58) composed of 16 peptides may be used (Joliot et al., Proc Natl Acad Sci USA 88: 1864-1868 (1991); Derossi et al., J Biol Chem 269, 10444-10450 (1994); Joliot, A. and A. Prochiantz, Nat. Cell Biol. 6(3): 189-96 (2004)), and in addition to the penetratin, peptide sequences having similar sequences and mechanisms are broadly called protein transduction domains (PTDs). It was disclosed that a mechanism of intracellular material transduction of such a PTD was performed by disrupting a cell membrane on a cell surface and delivering a material into the cell, or by accumulating a material in an endosome through endocytosis caused by electrostatic interaction between a negative charge of various glycans of a membrane protein present on the cell surface and a positive charge of basic amino acid residues constituting the PTD to be delivered into the cell, not by directly permeating a material into the cell membrane (J. S. Wadia, et al., Nat. Med. 10: 310-315 (2004); I. Nakase, et. al. Biochemistry 46: 492-501 (2007); H. L. Amand, et al., Biochim. Biophys. Acta (2011)). However, such a material transduction mechanism of the PTD has difficulty in transducing materials such as peptides, proteins, nucleic acids, etc. into a deep tissue in a living body. Particularly, peptides or proteins are accumulated in an endosome, and when binding to lysosomes in the cell, easily degraded by a protease of the lysosome. Accordingly, when the peptides or proteins are transduced in a sufficiently high concentration using the PTD, an effective component capable of acting on a target in a cytoplasm can be emitted from the endosome, which becomes a problem occurring in the protein transduction using the PTD (F. Milletti, Drug Discovery Today 17: 850-860 (2012)).

Later, in the 2000s, MTS (AAVLLPVLLAAP; SEQ ID NO: 59) derived from a signal peptide of a fibroblast growth factor (FGF) was synthesized and manufactured (DaeWoong Jo et al., Nat. Biotech. Vol. 19, 2001). The MTS is composed of 12 hydrophobic amino acids, in which one valine and two leucines are present between a sequence continuously having two alanines, and a proline is included, and has quite different characteristics from the conventional PTD. In addition, recently, as a more improved transduction domain, a new cell membrane permeable peptide having more improved efficiency of delivering materials into cells than the PTD and MTS and different structural and electrostatic characteristics was developed, and the peptide was a macromolecule transduction domain (MTD) (refer to WO 2008/093982).

When the MTD, which was technology developed by the inventors, is used, unlike the transduction into an HIV-TAT cell, endocytosis and energy are not needed in the intracellular transduction of a material, and rigidity and integrity of the cell membrane for direct interaction with the cell membrane serve as important factors, and thus continuous transduction between cells can also be performed. For this reason, the MTD has a high efficiency of delivering a target protein into a cell, and enables deliver into a deep tissue in a living body, compared to TAT, which is a conventional cell membrane permeable peptide. In addition, a hydrophobic MTD derived from a signal sequence of a secretory protein or a cell membrane protein is manufactured by modifying a sequence of a hydrophobic region of a signal peptide largely composed of three parts including a hydrophobic region at an N-terminus and secreted-protein cleavage sites at a C-terminus, the hydrophobic region forming a helix structure to have a cell-membrane-targeting activity. The MTD is directly permeated through the cell membrane without damage to a cell, and allows macromolecules such as proteins to be delivered into the cell to exhibit their own functions.

However, since the MTD is usually composed of hydrophobic amino acids, and thus decreased in physical properties and availability, when manufactured in connection with a strongly-hydrophobic peptide or protein, the MTD may be precipitated when melted under a general buffer condition at a predetermined concentration or more, or according to a characteristic of a transducing material. Accordingly, combination with the MTD, which is not precipitated within a concentration range to be used and exhibits optimum permeability and activity in consideration of characteristics of a material to be transduced, may also be needed.

Therefore, the inventors developed a new cell membrane permeable domain having improved cell membrane permeability through deletion or modification on an amino acid sequence, or chimeric fusion, to improve physical properties and availability of the conventional MTD and increase cell membrane permeability, and confirmed an intracellular transduction effect thereof, thereby proving a more improved effect than the conventional MTD. Thus, the present invention was completed.

DISCLOSURE

Technical Problem

The present invention was invented to develop the above-described peptide having a more excellent cell permeability by modifying an amino acid sequence of the conventional MTD peptide, and is directed to providing a modified MTD having improved cell membrane permeability and physical properties due to deletion, modification, or chimeric fusion to an amino acid sequence of the conventional MTD, and a polynucleotide encoding the modified MTD.

The present invention is also directed to providing a method of genetically engineering a biologically active molecule using the modified MTD to have cell permeability, and a method of inputting a biologically active molecule into a cell using the modified MTD.

However, technical objects to be achieved in the present invention are not limited to the above-described objects, and other objects which will not be described will be clearly understood from the following descriptions by those of ordinary skill in the art.

Technical Solution

Aspects of the present invention provide a peptide represented by Formula 1, in which A1 is methionine (M, Met); A2 is an amino acid selected from the group consisting of arginine (R, Arg), histidine (H, His) and lysine (K, Lys); and MTD has an amino acid sequence selected from the group consisting of SEQ. ID. NOs: 1 to 7:

A1-A2-MTD; and         [Formula 1]

a polynucleotide encoding the peptide.

In one embodiment of the present invention, the peptide mediates transport of a biologically active molecule into a cell, and has an amino acid sequence selected from the group consisting of SEQ. ID. NOs: 15 to 35.

In another embodiment of the present invention, the polynucleotide has a base sequence selected from the group consisting of SEQ. ID. NOs: 36 to 56.

In one embodiment of the present invention, the amino acid sequence of SEQ. ID. NO: 15 may be encoded with the sequence of SEQ. ID. NO: 36, but the present invention is not limited thereto.

In another embodiment of the present invention, the amino acid sequence of SEQ. ID. NO: 16 may be encoded with the polynucleotide sequence of SEQ. ID. NO: 37, but the present invention is not limited thereto.

In still another embodiment of the present invention, the amino acid sequence of SEQ. ID. NO: 17 may be encoded with the polynucleotide sequence of SEQ. ID. NO: 38, but the present invention is not limited thereto.

In yet another embodiment of the present invention, the amino acid sequence of SEQ. ID. NO: 18 may be encoded with the polynucleotide sequence of SEQ. ID. NO: 39, but the present invention is not limited thereto.

In yet another embodiment of the present invention, the amino acid sequence of SEQ. ID. NO: 19 may be encoded with the polynucleotide sequence of SEQ. ID. NO: 40, but the present invention is not limited thereto.

In yet another embodiment of the present invention, the amino acid sequence of SEQ. ID. NO: 20 may be encoded with the polynucleotide sequence of SEQ. ID. NO: 41, but the present invention is not limited thereto.

In yet another embodiment of the present invention, the amino acid sequence of SEQ. ID. NO: 21 may be encoded with the polynucleotide sequence of SEQ. ID. NO: 42, but the present invention is not limited thereto.

In yet another embodiment of the present invention, the amino acid sequence of SEQ. ID. NO: 22 may be encoded with the polynucleotide sequence of SEQ. ID. NO: 43, but the present invention is not limited thereto.

In yet another embodiment of the present invention, the amino acid sequence of SEQ. ID. NO: 23 may be encoded with the polynucleotide sequence of SEQ. ID. NO: 44, but the present invention is not limited thereto.

In yet another embodiment of the present invention, the amino acid sequence of SEQ. ID. NO: 24 may be encoded with the polynucleotide sequence of SEQ. ID. NO: 45, but the present invention is not limited thereto.

In yet another embodiment of the present invention, the amino acid sequence of SEQ. ID. NO: 25 may be encoded with the polynucleotide sequence of SEQ. ID. NO: 46, but the present invention is not limited thereto.

In yet another embodiment of the present invention, the amino acid sequence of SEQ. ID. NO: 26 may be encoded with the polynucleotide sequence of SEQ. ID. NO: 47, but the present invention is not limited thereto.

In yet another embodiment of the present invention, the amino acid sequence of SEQ. ID. NO: 27 may be encoded with the polynucleotide sequence of SEQ. ID. NO: 48, but the present invention is not limited thereto.

In yet another embodiment of the present invention, the amino acid sequence of SEQ. ID. NO: 28 may be encoded with the polynucleotide sequence of SEQ. ID. NO: 49, but the present invention is not limited thereto.

In yet another embodiment of the present invention, the amino acid sequence of SEQ. ID. NO: 29 may be encoded with the polynucleotide sequence of SEQ. ID. NO: 50, but the present invention is not limited thereto.

In yet another embodiment of the present invention, the amino acid sequence of SEQ. ID. NO: 30 may be encoded with the polynucleotide sequence of SEQ. ID. NO: 51, but the present invention is not limited thereto.

In yet another embodiment of the present invention, the amino acid sequence of SEQ. ID. NO: 31 may be encoded with the polynucleotide sequence of SEQ. ID. NO: 52, but the present invention is not limited thereto.

In yet another embodiment of the present invention, the amino acid sequence of SEQ. ID. NO: 32 may be encoded with the polynucleotide sequence of SEQ. ID. NO: 53, but the present invention is not limited thereto.

In yet another embodiment of the present invention, the amino acid sequence of SEQ. ID. NO: 33 may be encoded with the polynucleotide sequence of SEQ. ID. NO: 54, but the present invention is not limited thereto.

In yet another embodiment of the present invention, the amino acid sequence of SEQ. ID. NO: 34 may be encoded with the polynucleotide sequence of SEQ. ID. NO: 55, but the present invention is not limited thereto.

In yet another embodiment of the present invention, the amino acid sequence of SEQ. ID. NO: 35 may be encoded with the polynucleotide sequence of SEQ. ID. NO: 56, but the present invention is not limited thereto.

Another aspect of the present invention provides a method of genetically engineering a biologically active molecule having cell permeability, which includes attaching a peptide having an amino acid sequence selected from the group consisting of SEQ. ID. NOs: 15 to 35 to a biologically active molecule.

In one embodiment of the present invention, the attachment is performed by attaching a biologically active molecule to a N-terminus, a C-terminus, or both termini of the peptide.

In another embodiment of the present invention, the attachment is performed by attaching amino acids of the peptide inversely arranged to a C-terminus of the biologically active molecule.

In still another embodiment of the present invention, the attachment is performed by peptide bonds or chemical bonds.

In yet another embodiment of the present invention, the chemical bond may be selected from disulfide bonds, diamine bonds, sulfide-amine bonds, carboxyl-amine bonds, ester bonds, and covalent bonds.

In yet another embodiment of the present invention, the biologically active molecule is selected from the group consisting of proteins, polypeptides, and peptides.

In yet another embodiment of the present invention, the biologically active molecule is selected from the group consisting of growth factors, enzymes, transcription factors, toxins, antigenic peptides, antibodies, and antibody fragments.

In yet another embodiment of the present invention, the biologically active molecule may be selected from enzymes, hormones, carrier proteins, immunoglobulins, antibodies, structural proteins, motor function proteins, receptors, signaling proteins, storage proteins, membrane proteins, transmembrane proteins, internal proteins, external proteins, secretory proteins, viral proteins, native proteins, glycoproteins, cleaved proteins, proteins having a disulfide bond, protein complexes, chemically modified proteins, and prions.

In yet another embodiment of the present invention, the biologically active molecule may be selected from the group consisting of nucleic acids, coding nucleic acid sequences, mRNAs, antisense RNA (microRNA or siRNA) molecules, carbohydrates, lipids and glycolipids.

In yet another embodiment of the present invention, the biologically active molecule is a therapeutic drug or a toxic compound.

Still another aspect of the present invention provides a method of transporting a biologically active molecule into a cell of an individual, which includes administering a biologically-active-molecule-attached amino acid sequence selected from the group consisting of SEQ. ID. NOs: 15 to 35 into the individual.

Advantageous Effects

A modified MTD of the present invention has considerably more excellent cell permeability of delivering a biologically active molecule into a cell than a conventional MTD, and effectively maintains an activity of the delivered biologically active molecule in the cell. Accordingly, the modified MTD of the present invention may be used in a drug delivery system, a recombinant protein vaccine or a drug for DNA/RNA therapy, methods for gene and protein therapies, production of a pharmaceutically or medically available protein, or a pharmaco-medical or pharmaceutical composition, and may also be very useful in development of new and modified drugs.

DESCRIPTION OF DRAWINGS

FIG. 1 depicts the results of analysis of the secondary structures of modified MTDs of the present invention using a PEP FOLD server program, specifically MTDs represented by SEQ ID NOs: 15, 22, 29, 16, 23, 30 and 17.

FIG. 2 depicts the results of analysis of the secondary structures of modified MTDs of the present invention using a PEP FOLD server program, specifically MTDs represented by SEQ ID NOs: 24, 31, 18, 25, 32, 19 and 26.

FIG. 3 depicts the results of analysis of the secondary structures of modified MTDs of the present invention using a PEP FOLD server program, specifically MTDs represented by SEQ ID NOs: 33, 6, 20, 27, 34, 7 and 21.

FIG. 4 depicts the results of analysis of the secondary structures of modified MTDs of the present invention using a PEP FOLD server program, specifically MTDs represented by SEQ ID NOs: 28 and 35.

MODES OF THE INVENTION

Figure 5:
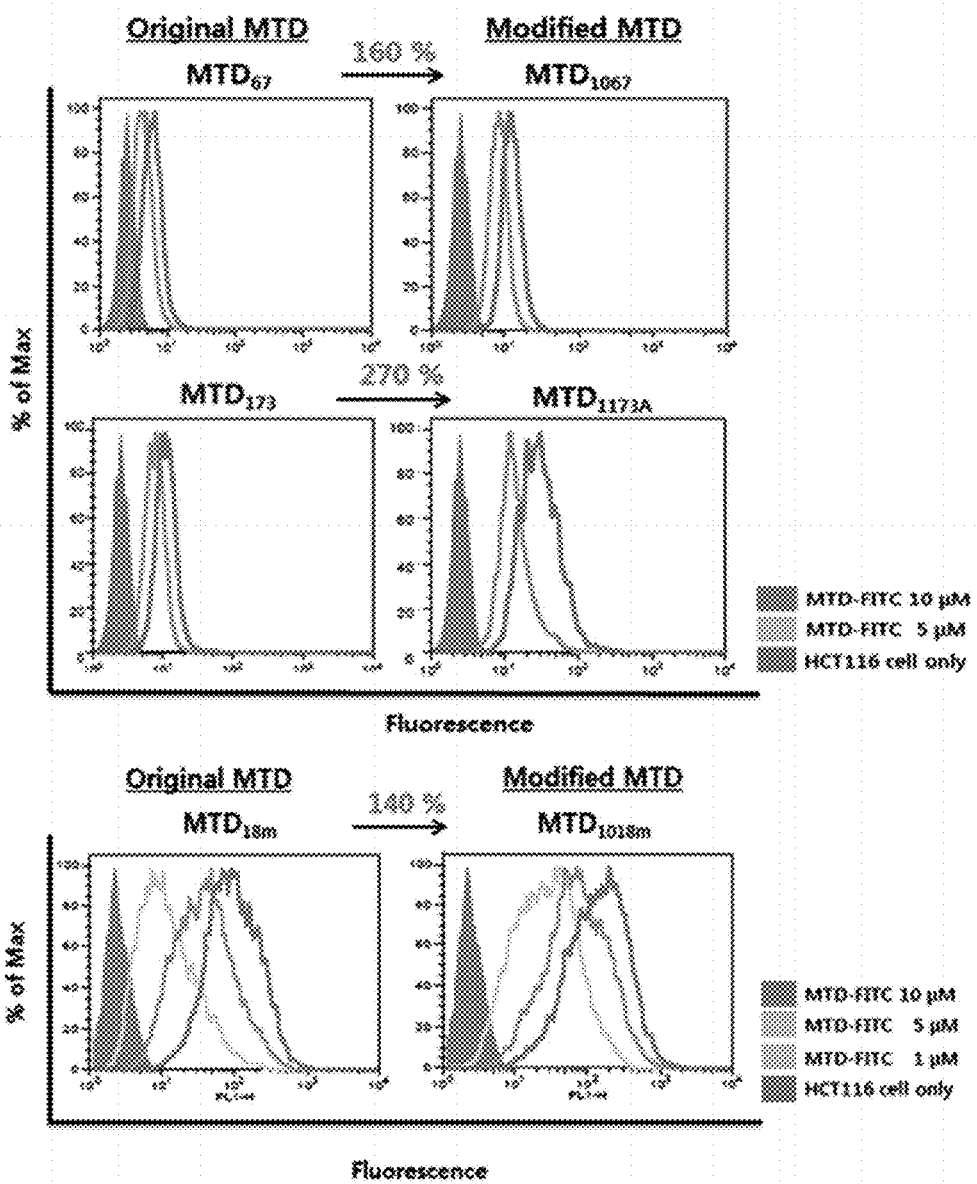
FIG. 5 is a result of analysis of quantitative cell permeability of a modified MTD of the present invention in human colorectal cancer cells through flow cytometry.

While low-molecular-weight synthetic compounds or natural compounds can be easily delivered into cells, macromolecules such as proteins, peptides, and nucleic acids are not permeated into a cell membrane, which is a double lipid membrane structure, due to large molecular weights. To overcome a shortcoming in which such macromolecules are not permeated through a plasma membrane of a cell, macromolecule intracellular transduction technology (MITT, Korean Patent Publication No. 10-2009-0103957) was developed.

Since a material transduction domain is composed of only hydrophobic amino acids, when the MITT is applied to negatively-charged carbohydrates such as heparan sulfate proteoglycans (HSPGs) and negatively-charged saccharides such as glycosaminoglycans and sialic acids, an ability to approach a cell membrane having a negative charge and hydrophilicity may be limited.

Since a signal peptide at an N-terminus used in the MITT is a short peptide indicating post-translational transport of a protein, a general structure of the signal peptide to various proteins is composed of an amphipathic domain including a starting codon, M, of the protein, and an amphipathic molecule is composed of two domains, for example, a hydrophilic (polar) domain and a hydrophobic (non-polar) domain. The inventors expected that in consideration of the amphipathic characteristic of the signal peptide, since roles of the two domains are obvious, the inventors estimated that continuity of the signal peptide would be well conserved.

However, when positively-charged amino acids are continued, or a sequence in which at least three positively-charged amino acids are included in a successive or five-amino-acid sequence is coupled with a hydrophobic peptide, the inventors estimated that the hydrophobic peptide would rather not directly permeat through a cell membrane and be transduced into a cell, but would be transduced into a cell through endocytosis, as the PTD did.

Based on such hypotheses, the inventors provided a new modified MTD more effectively delivering a biologically active molecule into a cell by increasing approachability to a cell membrane having a negative charge by applying one or two hydrophilic (polar) amino acids having a positive charge to a conventionally-invented hydrophobic MTD, and thus the present invention was completed.

The present invention provides a peptide represented by Formula 1, in which A1 is methionine (M, Met); A2 is an amino acid selected from the group consisting of arginine (R, Arg), histidine (H, His) and lysine (K, Lys); and an MTD has an amino acid sequence selected from the group consisting of SEQ. ID. NOs: 1 to 7:

A1-A2-MTD; and [Formula 1]

a polynucleotide encoding the peptide.

The peptide mediates transport of a biologically active molecule into a cell, and exhibits excellent cell permeability, compared to the MTD disclosed in Korean Patent Publication No. 10-2009-0103957. In the present invention, the peptide is called as a "modified MTD."

The peptide may have an amino acid sequence selected from the group consisting of SEQ. ID. NOs: 15 to 35, but the present invention is not limited thereto.

The peptide preferably has one of sequences quantified to allow relative comparison among 193 MTDs developed in Korean Patent Publication No. 10-2009-0103957, and the selected one satisfies, though the present invention is not limited thereto, the following conditions:

1) proline is in the middle of the sequence; 2) a value obtained by evaluating probability of inducing extracellular secretion using Signal P program with respect to each domain is 60% or more; 3) an aliphatic index evaluated using a Protparam program (refer to <http://web.expasy.org/protparam/>) is within 100 to 300; 4) flexibility evaluated using a Protscale (Average flexibility) program (refer to <http://web.expasy.org/protscale/>) is 0.36 or more; 5) a hydropathicity evaluated using the Protparam program is 3.0 or less; 6) an instability index evaluated using the Protparam program is within 30 to 60; and 7) a polarity evaluated using the Protscale (polarity) program is 0.1 or more.

The amino acid sequence of SEQ. ID. NO: 1 may be encoded with the polynucleotide sequence of SEQ. ID. NO: 8, but the present invention is not limited thereto.

The amino acid sequence of SEQ. ID. NO: 2 may be encoded with the polynucleotide sequence of SEQ. ID. NO: 9, but the present invention is not limited thereto.

The amino acid sequence of SEQ. ID. NO: 3 may be encoded with the polynucleotide sequence of SEQ. ID. NO: 10, but the present invention is not limited thereto.

The amino acid sequence of SEQ. ID. NO: 4 may be encoded with the polynucleotide sequence of SEQ. ID. NO: 11, but the present invention is not limited thereto.

The amino acid sequence of SEQ. ID. NO: 5 may be encoded with the polynucleotide sequence of SEQ. ID. NO: 12, but the present invention is not limited thereto.

The amino acid sequence of SEQ. ID. NO: 6 may be encoded with the polynucleotide sequence of SEQ. ID. NO: 13, but the present invention is not limited thereto.

The amino acid sequence of SEQ. ID. NO: 7 may be encoded with the polynucleotide sequence of SEQ. ID. NO: 14, but the present invention is not limited thereto.

The polynucleotide of the present invention may be a type of RNA or DNA, and the DNA includes cDNA and synthetic DNA. The DNA may be single- or double-stranded. If the DNA is single-stranded, it may be a coding strand or a non-coding (antisense) strand. The coding sequence may be the same as a base sequence selected from SEQ. ID. NOs: 36 to 56, or a different coding sequence. The coding sequences are obtained by degeneracy or redundancy of genetic codes, and encode the same polypeptides.

The polynucleotide of the present invention also includes a variant of the above-described polynucleotide, which encodes a fragment, analog, or derivative of the polynucleotide characterized by deduced amino acid sequences of SEQ. ID. NOs: 15 to 35. The variant of the polynucleotide may be a naturally generated allelic variant of the polynucleotide or a non-naturally-generated variant of the polynucleotide.

The polynucleotide of the present invention may have a naturally generated allelic variant of a coding sequence characterized by a base sequence selected from SEQ. ID. NOs: 36 to 56. The allelic variant is an alternate form of a polybase sequence having substitution, deletion or addition of at least one nucleotide, with no substantially change in a function of an encoded polynucleotide.

It is well known in the art that a single amino acid may be encoded by at least one nucleotide codon, and the polynucleotide may be easily modified to manufacture an alternate polynucleotide encoding the same peptide. Accordingly, in another embodiment of the present invention, the polynucleotide includes an alternate base sequence encoding a peptide including the above-described amino acid sequence. A nucleic acid molecule encoding a peptide including the claimed amino acid sequence includes the claimed sequence and a base sequence encoding an arbitrary combination of arbitrary amino acids located at an N-terminus or a C-terminus of the claimed amino acid sequence.

Another aspect of the present invention provides a method of genetically engineering a biologically active molecule to have cell permeability using the modified MTD.

A therapeutic use of the biologically active molecule is often limited by low cell permeability. Although the biologically active molecules have been shown to be taken up by cell via an intracellular endocytic process, the molecules that entert the cell in this manner are usually trapped in an intracellular endocytic vesicle and degraded in lysosomes.

The modified MTD of the present invention seems to have more effective cell permeability than a conventional MTD. The modified MTD of the present invention may be provided in the form of a kit, which includes required components known to one of ordinary skill in the art to facilitate linking of a peptide to a target polypeptide. Subsequently, a target protein attached to the modified MTD in this manner may be delivered in vitro or in vivo to the cell for intracellular endocytosis.

The above-described polynucleotide may be inserted into a protein expression vector to produce a protein which can be delivered into a cell from an outside thereof through the action of the above-described modified MTD.

An expression vector is genetically engineered to incorporate a nucleic acid sequence encoding a MTD in an orientation either N-terminal and/or C-terminal to a nucleic acid sequence encoding a peptide, polypeptide, protein domain, or full-length protein of interest as a biologically active molecule, and in the correct reading frame so that a recombinant protein consisting of the macromolecule transduction domain and the target biologically active molecule may be expressed. Expression vectors may be chosen from among those readily available for use in prokaryotic or eukaryotic expression systems.

As used in the present invention, an MTD is a macromolecule transduction domain that directs intracellular transport of a target protein from the exterior to the interior of a cell, and the modified MTD has more enhanced cell permeability than the conventional MTD. In another embodiment of the present invention, the modified MTD may include an alternate sequence mediating import of a peptide or a polypeptide into a cell through a cell membrane.

A target protein is a protein which normally exhibits less than optimal permeability through the cell membrane, but which, when attached either N-terminal and/or C-terminal to the modified MTD of the present invention, is transported from the exterior to the interior of the cell.

The target protein may have a cleavage site between the modified MTD, and the target polypeptide, protein domain, or full-length protein, and the cleavage site may alternatively be a factor X site or another site that is known to one of ordinary skill in the art relate to the cleavage of the recombinant protein to physically remove the modified MTD from the subject peptide or polypeptide.

As used in the present invention, the term "biologically active molecule" includes any molecule which, if imported into a cell, is capable of exhibiting a biological effect. Since very large proteins having molecular weights ranging from about 100,000 to about 1 million are exported by cells (e.g., antibodies, fibrinogen, and macroglobulin), very large proteins can be imported into cells by the method of the present invention.

Examples of biologically active molecules include, but are not limited to, proteins, polypeptides, and peptides, which include functional domains of biologically active molecules, such as growth factors, enzymes, transcription factors, toxins, antigenic peptides (for vaccines), antibodies, and antibody fragments. Additional examples of biologically active molecules include nucleic acids, such as plasmids, coding nucleic acid sequences, mRNAs and antisense RNA molecules, carbohydrates, lipids, and glycolipids. Further examples of biologically active molecules include those for diagnosing, treating and/or preventing a disease, in particular those with low cell membrane permeability. Some examples of these therapeutic agents include cancer drugs, such as Daunorubicin, and toxic chemicals which, because of the lower dosage that can be used when administered by this method, can now be more safely administered. Yet another example of a biologically active molecule is an antigenic peptide. Antigenic peptides can be administered to provide immunological protection when imported by cells involved in the immune response. Other examples include immunosuppressive peptides (e.g., peptides that block autoreactive T cells, which are known in the art). Numerous other examples will be apparent to the skilled artisan.

Representative examples of the biologically active molecule suitable for the present invention may include enzymes, hormones, transport proteins immunoglobulin or an antibodies, structural proteins, motor function proteins, receptors, signaling proteins and storage proteins in terms of their function; and membrane or transmembrane proteins, internal proteins, external or secret proteins, virus proteins, native proteins, glycoproteins, cleaved proteins, proteins with disulfide bonds, protein complexes, chemically modified proteins and prions in terms of their location and roles.

Standard recombinant nucleic acid methods can be used to express a genetically engineered recombinant protein. The nucleic acid sequence encoding the modified MTD of the present invention may be cloned in a nucleic acid expression vector having suitable signaling and processing sequences and regulatory sequences for transcription and translation, and a protein may be synthesized using an automated organic synthetic method. A method for synthesizing a protein is disclosed in the literature, for example, [Methods in Enzymology, Volume 289: Solid-Phase Peptide Synthesis by Gregg B. Fields (Editor), Sidney P. Colowick, Melvin I. Simon (Editor), Academic Press (1997)].

In order to obtain high level expression of a cloned gene or nucleic acid, such as a cDNA encoding a MTD peptide, a MTD sequence is typically subcloned into an expression vector that contains a strong promoter for directing transcription, a transcription/translation terminator, and, in the case of a nucleic acid encoding a protein, a ribosome binding site for translational initiation. Suitable bacterial promoters are well known in the art, and are disclosed in the literature [Sambrook & Russell, Molecular Cloning: A Laboratory Manual, 3d Edition, Cold Spring Harbor Laboratory, N.Y. (2001); and Ausubel et al., Current Protocols in Molecular Biology, Greene Publishing Associates and Wiley Interscience, N.Y. (1989)]. Bacterial expression systems for expressing the modified MTD of the present invention are available in, for example, E. coli, Bacillus sp., and Salmonella (Palva et al., Gene 22: 229-235 (1983); Mosbach et al., Nature 302: 543-545 (1983)). Kits for such expression systems are commercially available. Eukaryotic expression systems for mammalian cells, yeast, and insect cells are well known in the art and are also commercially available. In another embodiment of the present invention, the eukaryotic expression vector may be an adenoviral vector, an adeno-associated vector, or a retroviral vector.

Generally, the expression vector for expressing the cell permeable recombinant protein prepared by attaching a protein to a N-terminus, a C-terminus or both termini of the modified MTD may include, regulatory sequences, including for example, a promoter operably attached to a sequence encoding the macromolecule transduction domain.

Non-limiting examples of inducible promoters that can be used include steroid-hormone responsive promoters (for example, ecdysone-responsive, estrogen-responsive, and glutacorticoid-responsive promoters), the tetracycline "Tet-On" and "Tet-Off" systems, and metal-responsive promoters. The construct can be introduced into an appropriate host cell, for example, a bacterial cell, yeast cell, insect cell, or tissue culture cell. The construct can also be introduced into embryonic stem cells to generate a transgenic organism as a model subject. Large numbers of suitable vectors and promoters are known to one of ordinary skill in the art, and are commercially available for generating the recombinant constructs of the present invention.

Known methods can be used to construct vectors containing the polynucleotide of the present invention and appropriate transcriptional/translational control signals. These methods include in vitro recombinant DNA techniques, synthetic techniques, and in vivo recombination/genetic recombination. For example, such techniques are disclosed in the literature [Sambrook & Russell, Molecular Cloning: A Laboratory Manual, 3d Edition, Cold Spring Harbor Laboratory, N.Y. (2001); and Ausubel et al., Current Protocols in Molecular Biology Greene Publishing Associates and Wiley Interscience, N.Y. (1989)].

Host cells suitable for producing a cell permeable recombinant protein include bacterial cells and eukaryotic cells (for example, fungal, insect, plant, and mammalian cells). Host cells can be disrupted by any convenient method, including freeze-thaw cycling, sonication, mechanical disruption, or the use of cell lysing agents. The literature [Scopes, Protein Purification: Principles and Practice, New York: Springer-Verlag (1994)] discloses a number of general methods for purifying recombinant (and non-recombinant) proteins. The methods can include, for example, ion-exchange chromatography, size-exclusion chromatography, affinity chromatography, selective precipitation, dialysis, and hydrophobic interaction chromatography. These methods can be adapted to devise a purification strategy for the cell permeable recombinant protein. If the cell permeable recombinant protein includes a purification handle, such as an epitope tag or a metal chelating sequence, affinity chromatography can be used to purify the protein greatly.

The amount of protein produced can be evaluated by detecting the macromolecule transduction domain directly (for example, using Western analysis) or indirectly (e.g., by assaying materials from, the cells for specific DNA binding activity, such as by electrophoretic mobility shift assay). Proteins can be detected prior to purification, during any stage of purification, or after purification. In some implementations, purification or complete purification may not be necessary.

The genetically engineered recombinant proteins prepared by the method of the present invention are cell permeable proteins and can be used as protein-based vaccines, particularly where killed or attenuated whole organism vaccines are impractical. The cell permeable proteins prepared by the method of the present invention can also be used for the treatment of various diseases, particularly, an immune disease or a cancer. Cell permeable proteins can be delivered to the interior of the cell, eliminating the need to transfect or transform the cell with a recombinant vector. The cell permeable proteins of the present invention can be used in vitro to investigate protein function or can be used to maintain cells in a desired state.

The modified MTD of the present invention can be used to deliver peptides, polypeptides, protein domains, or proteins to the interior of a target cell either in vitro or in vivo. The modified MTD can be attached to the target protein through a peptide linkage formed by the expression of the recombinant protein from a recombinant DNA or RNA molecule or can be attached to the target protein by means of a linker covalently attached to the MTD. A covalent linkage can be used to attach the modified MTD of the present invention to a non-protein molecule, such as a polynucleotide, for import into the cell.

The method of genetically engineering proteins with cell membrane permeability according to the present invention provides a means for delivering therapeutic protein products into a cell. Combination of the present invention with previously described methods of extracellular protein delivery provides a method of delivering proteins for import into a cell in a stabilized, functional form in a controlled-release fashion.

Polypeptides are produced using an appropriate expression vector and an expression system. Cell permeability is conferred upon the protein or polypeptide by the expression of a recombinant protein with the MTD located N-terminal and/or C-terminal to the expressed polypeptide. The less stable proteins are stabilized by methods known to one of ordinary skill in the art and described previously. Delivery to the extracellular environment is accomplished by providing the stabilized recombinant protein in an appropriate carrier, such as microsphere carriers. The protein of choice will dictate the appropriate vector and expression system, as well as the appropriate stabilization and delivery techniques. A person of ordinary skill in the art of drug delivery systems can choose the appropriate techniques from among those described.

As used in the present invention, the term "cell membrane" refers to a lipid-containing barrier which separates cells or groups of cells from the extracellular space. Cell membranes include, but are not limited to, plasma membranes, cell walls, intracellular organelle membranes, such as the mitochondrial membrane, nuclear membranes, and the like.

As show in the present invention, the term "biologically active molecule" refers to compounds or molecules that are capable of eliciting or modifying a biological response in a system. Non-limiting examples of biologically active molecules include antibodies (for example, monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, siRNA, miRNA, RNAi inhibitors, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers. In certain embodiments, the term biologically active molecule is used interchangeably with the term "macromolecule".

As used in the present invention, the term "macromolecule" refers to large molecules (molecular weight greater than 1000 daltons) exemplified by, but not limited to, peptides, proteins, and oligonucleotides and polynucleotides of biological or synthetic origin.

As used in the present invention, the term "peptide" refers to a compound made up of a single chain of D- or L-amino acids or a mixture of D- and L-amino acids joined by peptide bonds. Preferably, peptides contain at least two amino acid residues and are less than about 50 amino acids in length.

As used in the present invention, the term "protein" refers to a compound that is composed of linearly arranged amino acids attached by peptide bonds, but in contrast to peptides, has a well-defined conformation. Proteins, as opposed to peptides, preferably contain chains of 50 or more amino acids.

As used in the present invention, the term "polypeptide" refers to a polymer of at least two amino acid residues and which contains one or more peptide bonds. Polypeptides encompass peptides and proteins, regardless of whether the polypeptide has a well-defined conformation.

As used in the present invention, the term "nucleic acid" refers to oligonucleotides or polynucleotides, such as deoxyribonucleic acid (DNA) and ribonucleic acid (RNA), as well as analogs of either RNA or DNA, for example made from nucleotide analogs any of which are in single or double stranded form.

Amino acid residues are herein referred to by their standard single-letter or three-letter notations or by their full names: A, Ala, alanine; C, Cys, cysteine; D, Asp, aspartic acid; E, Glu, glutamic acid; F, Phe, phenyl alanine; G, Gly, glycine; H, His, histidine; I, Ile, isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; and Y, Tyr, tyrosine.

As used in the present invention, the term "macromolecule transduction domain (MTD)" refers to a peptide that facilitates the transport of macromolecules into a cell.

Unless defined otherwise, all technical and scientific terms used herein have the same meaning as commonly understood by one of ordinary skill in the art to which this invention belongs. Although any method and material similar or equivalent to those described herein can also be used in the practice or testing of the present invention, specific methods and materials are now described. All publications mentioned herein are incorporated herein by reference in their entirety to disclose and describe the methods and/or materials in connection with which the publications are cited. It must be noted that as used herein and in the appended claims, the singular forms "a," "an," and "the" include plural referents unless the context clearly dictates otherwise.

In an exemplary embodiment of the present invention, the inventors proved that a structural characteristic of a macromolecule transduction domain (MTD) disclosed in the previous patent relating to a cell permeable peptide derived from a signal peptide (Korean Patent Publication No. 10-2009-0103957: NOVEL MACROMOLECULE TRANSDUCTION DOMAINS AND METHODS FOR IDENTIFICATION AND USES THEREOF) is not destroyed using a sequence fused with an N-terminus sequence of an EGFP fluorescent protein by a PEP FOLD server service program, which can be verified online (refer to FIGS. 1 to 4).

In still another exemplary embodiment of the present invention, a complex formed by linking an FITC fluorescent material to an MTD was prepared to quantitatively determine cell permeability of the MTD peptide, and cells were treated with the FITC-MTD peptide and then analyzed using a flow cytometer. As a result, a higher fluorescent signal was shown in a modified MTD of the present invention, compared to the conventional MTD, and moreover, an effect of penetrating the modified MTD into a cell was proved by confirming that the MTD more effectively delivered FITC into cells than a protein transduction domain (PTD).

In still another exemplary embodiment of the present invention, cell permeability and intracellular localization were visualized using a complex prepared by linking an FITC fluorescent material to an MTD through confocal microscopy. As a result, higher cell permeability was shown in the modified MTD than the conventional MTD, which was the same as the result of flow cytometry, and it was also confirmed that cell permeability was higher in the MTD than in the PTD.

In addition, in yet another exemplary embodiment of the present invention, LacZ siRNA-Cy3 fused with MTD2173A was intravenously administered to mice to visualize lung tissue permeability through confocal microscopy, and a decrease in production of β-galactosidase protein consistently expressed in a mouse by LacZ siRNA was confirmed by observing a tissue of an enucleated lung stained with X-gal using a microscope, proving long-term penetration of the modified MTD into the tissue.

Hereinafter, exemplary Examples will be presented to help with understanding of the present invention. However, the following Examples are merely provided such that the present invention can be more fully understood, not to limit the scope of the present invention.

Example 1

Selection of MTD Peptide to Invent Modified MTD

The inventors selected a sequence of a target MTD to enhance transducibility in a sequence satisfying the following conditions of sequences quantified for relative comparison among 193 MTDs developed in Korean Patent Publication No. 110-2009-0103957 which is the technology previously developed by the inventors.

Conditions for the selection are as follows:

1) Among sequences of macromolecule transduction domain, a sequence of MTD in which proline was located in the middle was selected.

2) Among sequences of macromolecule transduction domain, a sequence of MTD having a high extracellular secretion-inducibility was selected.

3) Among sequences of macromolecule transduction domain, a sequence of MTD satisfying a specific level of an aliphatic index, which is a factor determining physiochemical characteristics of the MTD, was selected.

4) Among sequences of macromolecule transduction domain, a sequence of MTD satisfying a specific level of flexibility, which is a factor determining physiochemical characteristics of the MTD, was selected.

5) Among sequences of macromolecule transduction domain, a sequence of MTD satisfying a specific level of hydropathicity, which is a factor determining physiochemical characteristics of the MTD, was selected.

6) Among sequences of macromolecule transduction domain, a sequence of MTD satisfying a specific level of an instability index, which is a factor determining physiochemical characteristics of the MTD, was selected.

7) Among sequences of macromolecule transduction domain, a sequence of MTD satisfying a specific level of polarity, which is a factor determining physiochemical characteristics of the MTD, was selected.

The above-described conditions will be described in detail.

To screen a specific representative sequence, as will be described in Step 1), a representative sequence was determined based on the presence and position of proline.

Among alanine, valine, proline, leucine and isoleucine that are amino acids constituting a sequence of the MTD, the proline having a short side chain sequence and a small size has an influence on a degree of freedom for forming a secondary structure of the amino acid sequence, and contributes to permeation of the MTD through a cell membrane. Among the MTDs disclosed in Korean Patent Publication No. 10-2009-0103957, entitled "NOVEL MACROMOLECULE TRANSDUCTION DOMAINS AND METHODS FOR IDENTIFICATION AND USES THEREOF", 49 MTDs having a proline in the middle of their amino acid sequence, and thus classified to have a high degree of freedom for forming a secondary structure of the amino acid sequence were determined.

Subsequently, in the MTD selected in Step 1), a sequence having a high extracellular secretion probability was selected. Some water-soluble proteins have a signal which can interact with a receptor mediating transport, and in signal-mediated transport, the protein has one or more signal sequences indicating a delivered target. Accordingly, assuming that higher similarity to the extracellular secretion-inducing sequence can improve transducibility, extracellular secretion inducibility was evaluated using a Signal P program. Probability between 10 and 90% with respect to each domain was evaluated, and in the MTD determined in Step 1), a sequence evaluated to have a probability of 60% or more was selected as a modified target sequence.

Subsequently, in the MTD selected in Step 2), as described in Step 3), a sequence satisfying a specific level of an aliphatic index, which is a factor determining a physiochemical characteristic of the MTD, was selected. The aliphatic index is a physical characteristic determining a total volume of a molecule determined by a carbon chain of a side chain of amino acids, and evaluated as a characteristic of modifying a structure of the cell membrane. The aliphatic index is determined by an original value of each amino acid sequence of the MTD and an average of the total sequence using a Protparam program (refer to <http://web.expasy.org/protparam/>). The Protparam program is a useful tool in visualizing a physical characteristic of a protein or peptide composed of amino acids, and a sequence evaluated to have an aliphatic index of 100 to 300 was selected as a representative sequence to improve transducibility.

Subsequently, in the MTD selected in Step 3), as described in Step 4), a sequence satisfying a specific level of flexibility, which is a factor determining a physiochemical characteristic of the MTD, was selected. The flexibility is a physiochemical characteristic referring to correlation between an amino acid at an N terminus and an amino acid at a C terminus of the MTD and a degree of freedom, and provides structural flexibility, and is involved with affinity to the cell membrane. The flexibility was evaluated according to a length of the amino acid sequence and a construction of a side chain sequence of the amino acid, using a Protscale (Average flexibility) program (refer to <http://web.expasy.org/protscale/>). The Protscale program was used as a tool for digitizing physical characteristics of a protein or a peptide composed of amino acids, and among the MTDs determined in Step 3), a sequence having a flexibility of 0.36 or more, which was evaluated using the Protscale (Average flexibility) program was selected as a representative sequence for improving transducibility.

Subsequently, in the MTD selected in Step 4), as described in Step 5), a sequence satisfying a specific level of hydropathicity, which is a factor determining a physiochemical characteristic of the MTD, was selected. The hydropathicity is a physiochemical characteristic determined by an original characteristic of an amino acid and considered as a characteristic determining a physical property, and it is known that serious agglomeration is caused when the hydropathicity is 3.0 or more. In addition, the hydropathicity was determined by an original value of the amino acid of the MTD and an average of the total sequence, and evaluated using the Protparam program. Accordingly, a sequence having a hydropathicity of 3.0 or less in the MTD selected in Step 4) of the evaluation results for hydropathicity having a value between 1.3 and 3.9 was determined as a representative sequence for modification.

Subsequently, in the MTD selected in Step 5), as described in Step 6), a sequence satisfying a specific level of an instability index of macromolecule transduction domains was determined. The instability index is a characteristic indicating stability of an amino acid sequence, determined by an arrangement order of amino acids on the sequence, and as the instability index increased, instability also increased. The instability index is a factor determining physiochemical characteristics of the MTD, considered as a characteristic having an influence on intracellular stability of the domain, and evaluated using the Protparam program. Accordingly, among MTDs having an instability index of 0 to 130, a sequence having an instability of 30 to 60 in the MTD determined in Step 5) was selected as a representative sequence for modification.

Subsequently, in the MTD selected in Step 6), as described in Step 7), a sequence satisfying a specific level of polarity of the MTD, which is a factor determining a physiochemical characteristic of the MTD, was determined. The polarity is a scale showing affinity to water, which is determined by a length of a carbon chain of components of an amino acid and the presence of a hydroxide group. The polarity is a characteristic determining a physical property of the MTD, as well as hydropathicity, and considered to have an influence on affinity to the cell membrane. The polarity is determined by an original value of the amino acid of the MTD and an average of the total sequence, and evaluated using the Protscale (polarity) program. Accordingly, among the MTDs determined in Step 6), a sequence evaluated to have a polarity of 0.1 or more using the Protscale (polarity) program was selected as a representative sequence for modification.

Particularly, a target MTD, JO-103 (SEQ. ID. NO: 3), for inventing a modified MTD among the MTDs disclosed in Korean Patent Publication No. 10-2009-0103957 was determined by the following process.

i) JO-103 of the MTDs known from Korean Patent Publication No. 10-2009-0103957, entitled "NOVEL MACROMOLECULE TRANSDUCTION DOMAINS AND METHODS FOR IDENTIFICATION AND USES THEREOF," was composed of a sequence of LALPVLLLA;

ii) had a probability of 90% in evaluation of extracellular secretion probability using a Singal P program;

iii) had an aliphatic index of 271, determined using the Protparam program;

iv) had a flexibility of 0.38, determined using the Protscale program;

v) had a hydrophobicity of 2.8, determined using the Protparam program;

vi) had an instability index of 52, determined using the Protparam program; and vii) had a polarity of 0.13, determined using the Protscale program.

Thus, it is known that JO-103 determined as the target sequence for improving transducibility is a target domain satisfying all of the 7 steps.

Through the same method, five target MTDs for inventing a modified MTD were selected, and particularly, the selected target MTDs were MTD JO-018 (SEQ. ID. NO: 1), MTD JO-067 (SEQ. ID. NO: 2), MTD JO-103 (SEQ. ID. NO: 3), MTD JO-159 (SEQ. ID. NO: 4) and MTD JO-173 (SEQ. ID. NO: 5).

Additional flexibility was ensured by changing a position of proline of MTD JO-173; and an intermediate peptide, MTD 173A (SEQ. ID. NO: 7), was manufactured. Since the MTD 173A manufactured in such a manner satisfied all of the 7-step selection conditions, it was also included in the target MTD sequence for inventing a modified MTD.

In addition, for JO-18 of the selected MTDs as targets, a sequence was substituted with an amino acid having a low hydropathicity, thereby deducing the intermediate peptide, MTD 18m (SEQ. ID. NO: 6), to improve a physical property. The MTD 18m also satisfied the 7-step selection conditions and thus was also included in the target MTD sequence for inventing a modified MTD.

Example 2

Invention of Modified MTD

For the 7 target MTDs selected in Example 1, 1 to 2 hydrophilic (polar) amino acids were added to be applied to a hydrophobic domain, thereby increasing approachability to a cell membrane, and thus producing a new modified MTD more efficiently delivering a biologically active molecule into a cell, and therefore a peptide represented by the following Formula was invented:

A1-A2-MTD;  [Formula 1]

Here, A1 is methionine (M, Met); A2 is an amino acid selected from the group consisting of arginine (R, Arg), histidine (H, H is) and lysine (K, Lys), which are positively-charged; and MTD is a 7-amino-acid sequence selected from the group consisting of SEQ. ID. NOs: 1 to 7 selected in Example 1.

The sequence of the modified MTD invented through Formula 1 is the same as one of the amino acid sequences described in SEQ. ID. NOs: 15 to 35, and a peptide is synthesized based on the invented amino acid sequence, thereby confirming cell permeability.

Example 3

Analysis of Secondary Structure of Modified MTD

A secondary structure of the modified MTD invented in Example 2 was analyzed using a PEP FOLD server program.

As a result, as shown in FIGS. 1 to 4, it was confirmed that the modified MTD invented in Example 2 did not damage a structural characteristic of the MTD disclosed in Korean Patent Publication No. 10-2009-0103957, entitled "NOVEL MACROMOLECULE TRANSDUCTION DOMAINS AND METHODS FOR IDENTIFICATION AND USES THEREOF," and maintained an α-helix structure increasing permeability of the cell membrane.

Example 4

Synthesis of Modified MTD

Synthesis of the modified MTD designed in Example 2 was performed by coupling one by one from C-term using Fmoc solid phase peptide synthesis (SPPS).

Particularly, first, a resin to which the first amino acid at the C-terminus of a peptide was attached was used. The available resin was used in synthesis by selecting a suitable resin selected from an $NH_2$-Lys(Dde)-2-chloro-trityl resin, an $NH_2$-Met-2-chloro-trityl resin, or an $NH_2$-Ser(tBu)-2-chloro-trityl resin when needed.

Second, all amino acid materials, in which N-termini were protected with Fmoc and residues were protected with Trt, Boc, t-Bu, etc. that were removed from all of acids, were used to synthesize the peptide (Fmoc-Ala-OH, Fmoc-Val-OH, Fmoc-Arg(Pbf)-OH, Fmoc-Thr(t-Bu)-OH, Fmoc-Ser(t-Bu)-OH, Fmoc-Lys(Boc)-OH, Fmoc-Pro-OH, Fmoc-Met-OH).

Third, Fmoc was removed by a reaction performed twice using 20% piperidine in DMF at room temperature for 5 minutes.

Fourth, DMF, MeOH, MC, and DMF were washed sequentially.

Fifth, to isolate the synthesized peptide from the resin and remove protecing groups of the residue, TFA/EDT/Thioanisole/TIS/H2O=90/2.5/2.5/2.5/2.5 was used (TFA=trifluoroacetic acid, EDT=1,2-ethanedithiol, TIS=triisopropylsilane). Finally, after purification through HPLC, identifying was performed using a mass spectrometer, and lyophilization was perfomed, thereby a modified MTD was obtained.

In addition, to synthesize a fluorescent material (FITC)-attached MTD, after MTD synthesis was performed by the above-described synthesis method, a lysine (K) was finally added to perform peptide synthesis, and then FITC was bound to a free amine residue of the lysine. The synthesized MTD-FITC was isolated from the resin, and purified by HPLC, and a molecular weight of the peptide was identified by a mass spectrometer and lyophilized, thereby preparing an MTD-FITC. Afterward, the synthesized modified MTD-FITC was dissolved in sterile distilled water to a concentration of 1 mM in a light shielding state, was dispensed in a small amount into a 1.5 mL centrifuge container, and was stored in freeze until it was used.

Example 5

Identification of In Vitro Cell Permeability of Modified MTD Using Flow Cytometry To identify in vitro cell permeability of the modified MTD of the present invention and a conventional MTD (a modified target MTD), flow cytometry was used.

Particularly, after 1, 5 or 10 μM of MTD was labeled with FITC, the synthesized sample was treated to a human colon cancer (HCT116, Cat No. CCL-247, ATCC, USA), and cultured for 4 hours. The HCT116 cells were cultured in a RPMI1640 medium containing 10% fetal bovine serum (FBS) and 1% penicillin/streptomycin (10,000 units penicillin and 10,000 mg/mL streptomycin, Invitrogen) in a humidified atmosphere with 5% $CO_2$ at 37° C. After the culture was completed, trypsine was treated to remove free MTD-FITC exposed to a cell membrane of the HCT116 cell to which each sample was treated, and the resulting cells were washed three times with cold phosphate buffer.

The washed cells were retrieved, and applied to a fluorescence-activated cell sorting (FACS) assay (FACS Calibur, Beckton-Dickinson, San Diego Calif., USA). For each sample, cells ($1 \times 10^4$) were analyzed using CellQues Pro cytometric analysis software to perform quantitative comparison and analysis for cell permeability of the modified MTD-FITC and the conventional MTD-FITC.

The analysis results are shown in FIG. 5, and particularly, in FIG. 5 showing flow cytometry results, a curve filled with grey indicates cell permeability of single cells, a green curve indicates cell permeability of 1 μM of a treated concentration group, an orange curve indicates cell permeability of 5 μM of a treated concentration group, and a red curve indicates cell permeability of 10 μM treated concentration group.

As shown in FIG. 5, it was seen that, comparing geometric means of 10 μM of MTD-FITC, the modified MTD had a high fluorescent signal of a minimum of 140% to a maximum of 270% of the conventional MTD, and even a low concentration of the modified MTD was enhanced in cell permeability in a similar level to that of a high concentration of the conventional MTD.

Accordingly, it was seen that the modified MTD invented for the present invention was considerably enhanced in plasma membrane permeability of cell, compared to the conventional MTD.

Example 6

Identification of In Vitro Cell Permeability of Modified MTD Using Flow Cell Cytometry (HEK293 Cell)

Additionally, for HEK293 cells derived from human embryonic kidney cells, in vitro cell permeability was identified through flow cell cytometry. Samples prepared by linking FITC to the modified MTD of the present invention and the previously known MTD, a scrambled peptide considered to have a low cell permeability and cell permeability, and a kFGF4-derived marcomolecule transduction sequence (MTS) having previously-investigated cell permeability were used as controls.

Particularly, 5 μM of the sample was treated to human embryonic kidney cells (HEK293), and cultured for 6 hours. The HEK293 cells were cultured in an RPMI1640 medium containing 10% fetal bovine serum (FBS) and 1% penicillin/streptomycin (10,000 units penicillin and 10,000 ng/mL streptomycin, Invitrogen) in a humidified atmosphere with 5% $CO_2$ at 37° C. After the culture was completed, trypsine was treated to remove free MTD-FITC exposed to a cell membrane of the HCT116 cell to which each sample was treated, and the resulting cells were washed three times with cold phosphate buffer.

The washed cells were retrieved, and applied to a fluorescence-activated cell sorting (FACS) assay (FACS Calibur, Beckton-Dickinson, San Diego Calif., USA). For each sample, cells ($1 \times 10^4$) were analyzed using the CellQues Pro cytometric analysis software to perform quantitative comparison and analysis for cell permeability of the modified MTD-FITC and the MTD-FITC in the prior art.

Figure 6:
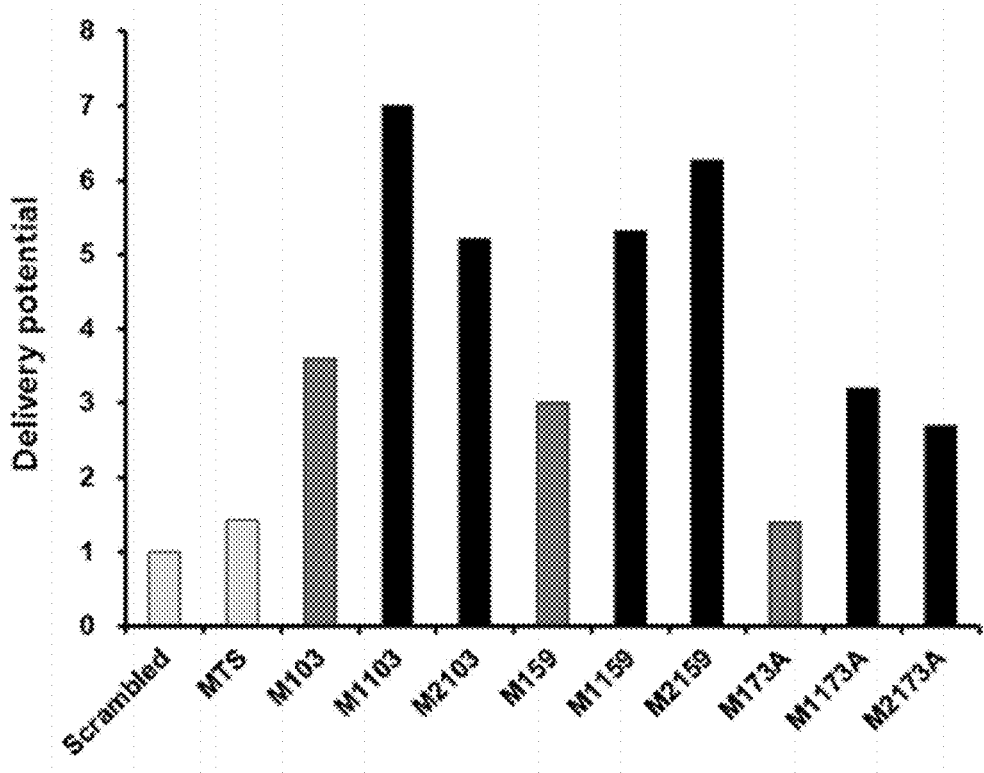
FIG. 6 is a result of analysis of quantitative cell permeability of a modified MTD of the present invention in human embryonic kidney cells through flow cytometry.

The analysis results are shown in FIG. 6, and as a result, it was confirmed that a JO-103 MTD peptide having the amino acid sequence of SEQ. ID. NO: 3 was enhanced in cell permeability 150 to 190% after modification, and a JO-159 MTD peptide having the amino acid sequence of SEQ. ID. NO: 4 was enhanced in cell permeability 180 to 210% after modification. In addition, in the case of an MTD peptide prepared by modifying a JO-173A MTD peptide having the amino acid sequence of SEQ. ID. NO: 7, it was confirmed that cell permeability was improved up to 190-230%.

Accordingly, it was seen that the modified MTD invented for the present invention was considerably enhanced in cell permeability, compared to the conventional MTD.

Example 7

Identification of In Vitro Cell Permeability of Modified MTD Using Confocal Laser Scanned Microscope To confirm improvement of functionality of the modified MTD based on the conventional MTD of the present invention, visible cell permeability was identified using a confocal laser scanned microscope with respect to skin-derived cells and cancer-derived cells.

7-1. Identification of Cell Permeability in Skin-Derived Cells

Immortalized human keratinocytes (HaCaT cells, Cat No. 300493, CLS, Germany) were used as skin-derived cells, and scrambled peptides having no cell permeability and Tat and MTS considered to have cell permeability were used as controls.

Particularly, before a test, HaCaT cells were cultured in a 12-well culture plate containing a glass cover slip for 24 hours. The HaCaT cells were cultured in a DMEM medium containing 10% fetal bovine serum (FBS), and 1% penicillin/streptomycin (10,000 units penicillin and 10,000 μg/mL streptomycin, invitrogen), in a humidified atmosphere with 5% $CO_2$ at 37° C. After 5 μM of peptides was treated to the HaCaT cells for 1 hour, the cells were fixed with 4% paraformaldehyde (PFA) at room temperature for 20 minutes to observe the cell permeability using a confocal microscope.

Figure 7:
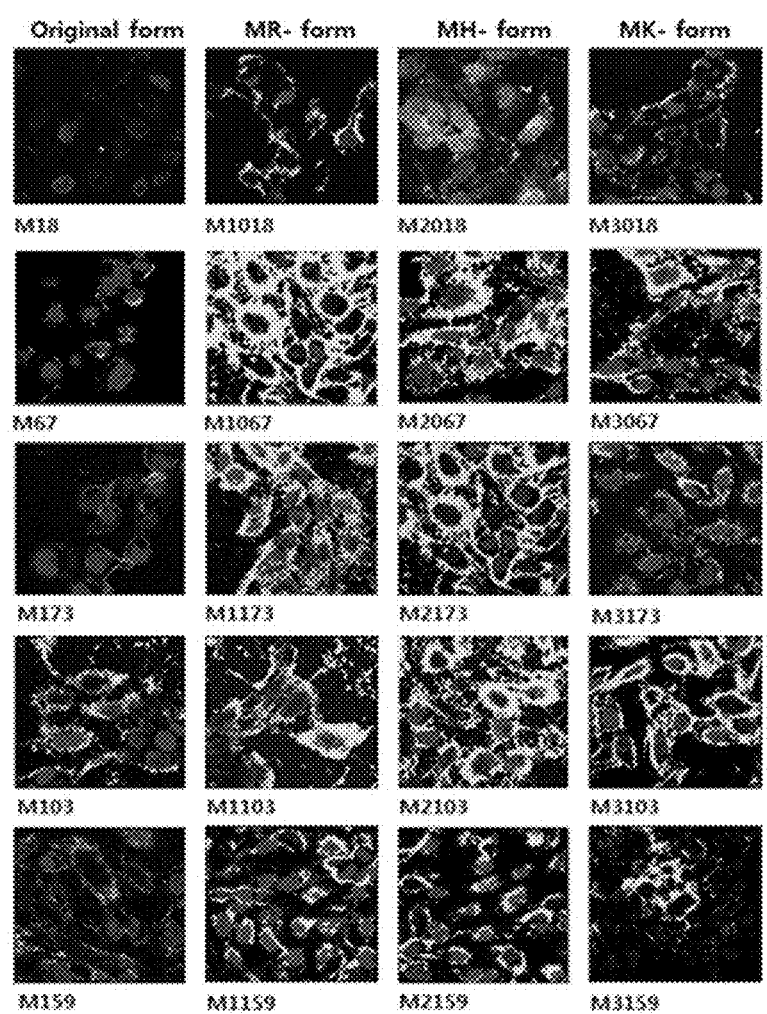
FIG. 7 depicts the results of observation of visible cell permeability of a modified MTD of the present invention in skin-originating keratinocytes through confocal laser scanning microscopy; MR-form: modified MTD represented by Formula A1-A2-MTD, in which A1 is methionine and A2 is arginine; MH-form: modified MTD represented by A1-A2-MTD, in which A1 is methionine and A2 is histidine; and MK-form: modified MTD represented by Formula A1-A2-MTD, in which A1 is methionine and A2 is lysine.
Figure 8:
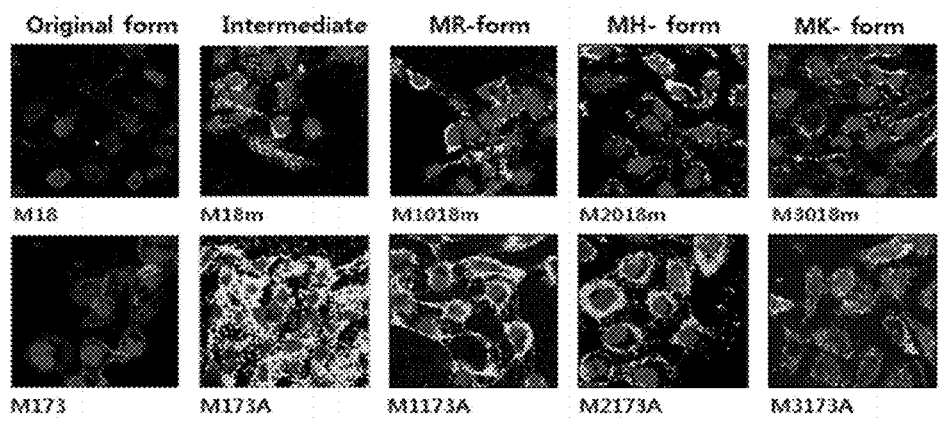
FIG. 8 depicts the results of observation of visible cell permeability of a modified MTD of the present invention in skin-originating keratinocytes through confocal laser scanning microscopy; MR-form: modified MTD represented by Formula A1-A2-MTD, in which A1 is methionine and A2 is arginine; MH-form: modified MTD represented by A1-A2-MTD, in which A1 is methionine and A2 is histidine; and MK-form: modified MTD represented by Formula A1-A2-MTD, in which A1 is methionine and A2 is lysine.
Figure 9:
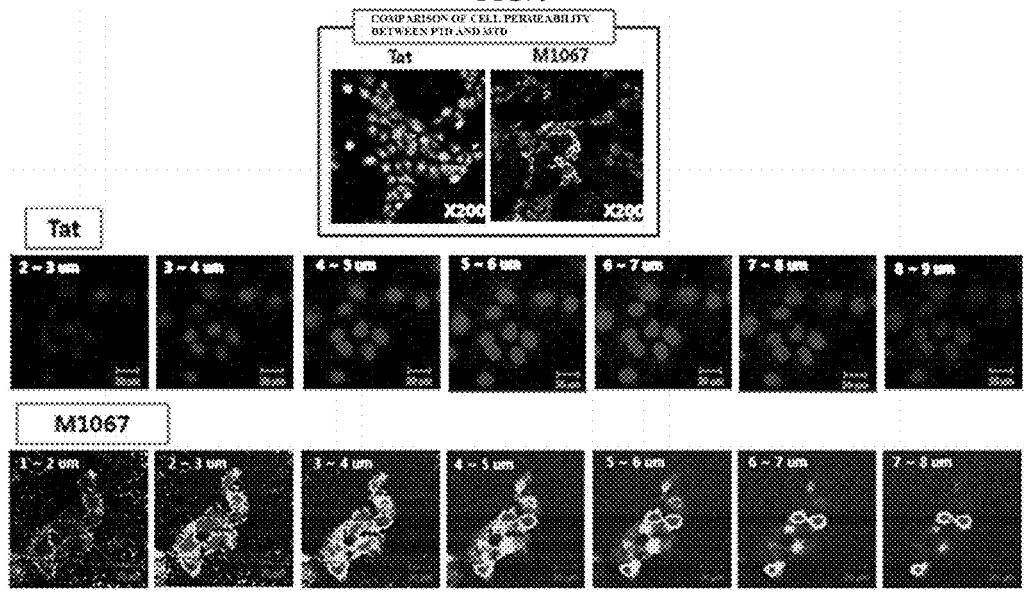
FIG. 9 depicts the results of observation of the comparison of cell permeability between PTD and MTD.

As a result, as shown in FIGS. 7 to 9, it was visualized that cell permeability of the modified MTD was considerably improved through modification of the peptides of the present invention.

7-2. Identification of Cell Permeability in Cervix Adenocarcinoma Cells

Cell permeability of HeLa cells (HeLa cell, Human cervix adenocarcinoma, Cat No. CCL-2, ATCC, USA) derived from Human cervix adenocarcinoma as cancer-derived cells was compared using a confocal microscope (Carl Zeisse, Germany).

Particularly, before a test, the HeLa cells were cultured in a 12-well culture plate with a glass cover slip for 24 hours. The HeLa cells were cultured in a DMEM medium containing 10% fetal bovine serum (FBS), and 1% penicillin/streptomycin (10,000 units penicillin and 10,000 μg/mL streptomycin, invitrogen), in a humidified atmosphere with 5% $CO_2$ at 37° C. After 5 μM of peptides was treated to the HaCaT cells for 1 hour, the cells were fixed with 4% paraformaldehyde (PFA) at room temperature for 20 minutes to observe the cell permeability using a confocal microscope.

To directly detect internalized MTD-FITC, the cells were washed three times with phosphoric acid buffer and 5 μM of 4',6-diamidino-2-phenylindole (DAPI), which is a nucleus fluorescence staining solution, was counter-stained. After 10-minute DAPI staining, the cells were washed three times with phosphoric acid buffer, and to conserve a fluorescent label of a protein, 20 µl of mounting media was dropped on a slide and observed. Transfer into a nucleus and cell permeability were identified by staining the MTD-FITC-treated cells through DAPI staining to facilitate distinction of an intracellular transfer part. In addition, an original form of the cell was observed using a nomarski filter with a confocal microscope, and FITC fluorescence and DAPI fluorescence were observed using a filter suitable for a fluorochrome.

Figure 10:
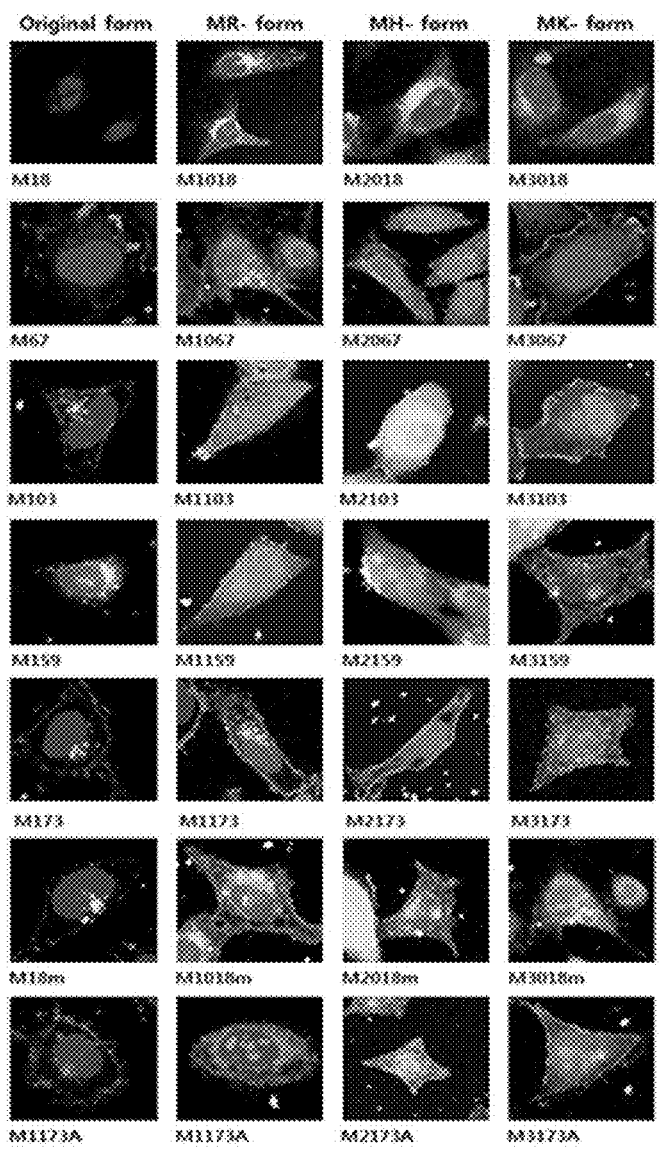
FIG. 10 is a result of observation of visible cell permeability of a modified MTD of the present invention in human cervical carcinoma cells through confocal laser scanning microscopy; MR-form: modified MTD represented by Formula A1-A2-MTD, in which A1 is methionine and A2 is arginine; MH-form: modified MTD represented by A1-A2-MTD, in which A1 is methionine and A2 is histidine; and MK-form: modified MTD represented by Formula A1-A2-MTD, in which A1 is methionine and A2 is lysine.

As a result, as shown in FIG. 10, it was seen that the modified MTDs have considerably higher intracellular transducibility than the conventional MTD peptide (18m, 67, 103, 159 and 173) used in the test. In addition, unlike the results for PTD (Tat) in which the peptide was attached to an outside of the cell membrane, it was confirmed that the modified MTDs (1018m, 1067, 1103, 1159, 1173A, 2103, and 2159) used in the test were apparently distributed into a cytoplasm, and thus considerable improvement in cell permeability of the newly invented modified MTD in the present invention was also visualized in cancer cells.

Example 8

Identification of Ex Vivo Epithelial Tissue Permeability of Modified MTD

To analyze ex vivo tissue permeability of the modified MTD of the present invention, in EpiOral epithelial models (MatTek, MA, USA), the conventional FITC-conjugated MTD (18m, 173) and the modified MTD (1018m and 1173A) were selectively treated, and visually observed by confocal microscopy (Carl Zeisse, Germany).

Particularly, one day before the test, the EpiOral epithelial models were cultured in a 12-well plate, each well containing 0.5 ml of a test medium provided by MatTek in a humidified atmosphere with 5% $CO_2$ at 37° C. for 15 hours. The next day, the media were exchanged with fresh media, 40 µl of MTDs having a concentration of 50 µM was treated on the EpiOral skin, and cultured in a humidified atmosphere with 5% $CO_2$ at 37° C. for 5 hours. The EpiOral epithelial model was fixed in 4% paraformaldehyde (PFA) for 15 hours or more, and a cryosection (6 µm) was prepared using a Microm cryosector (Microm HM520 cryostat, Thermo) and put on a glass slide to form a slide for microscopy. The formed slide was treated with phosphoric acid buffer for 10 minutes to wash a fragment, and treated with a 0.5 mM DAPI solution for 5 minutes to stain a nucleus in a tissue. The stained tissue was washed again three times for 10 minutes with phosphoric acid buffer, fixed to a slide using mounting media, and observed by confocal microscopy. The results are shown in FIG. 11.

Figure 11:
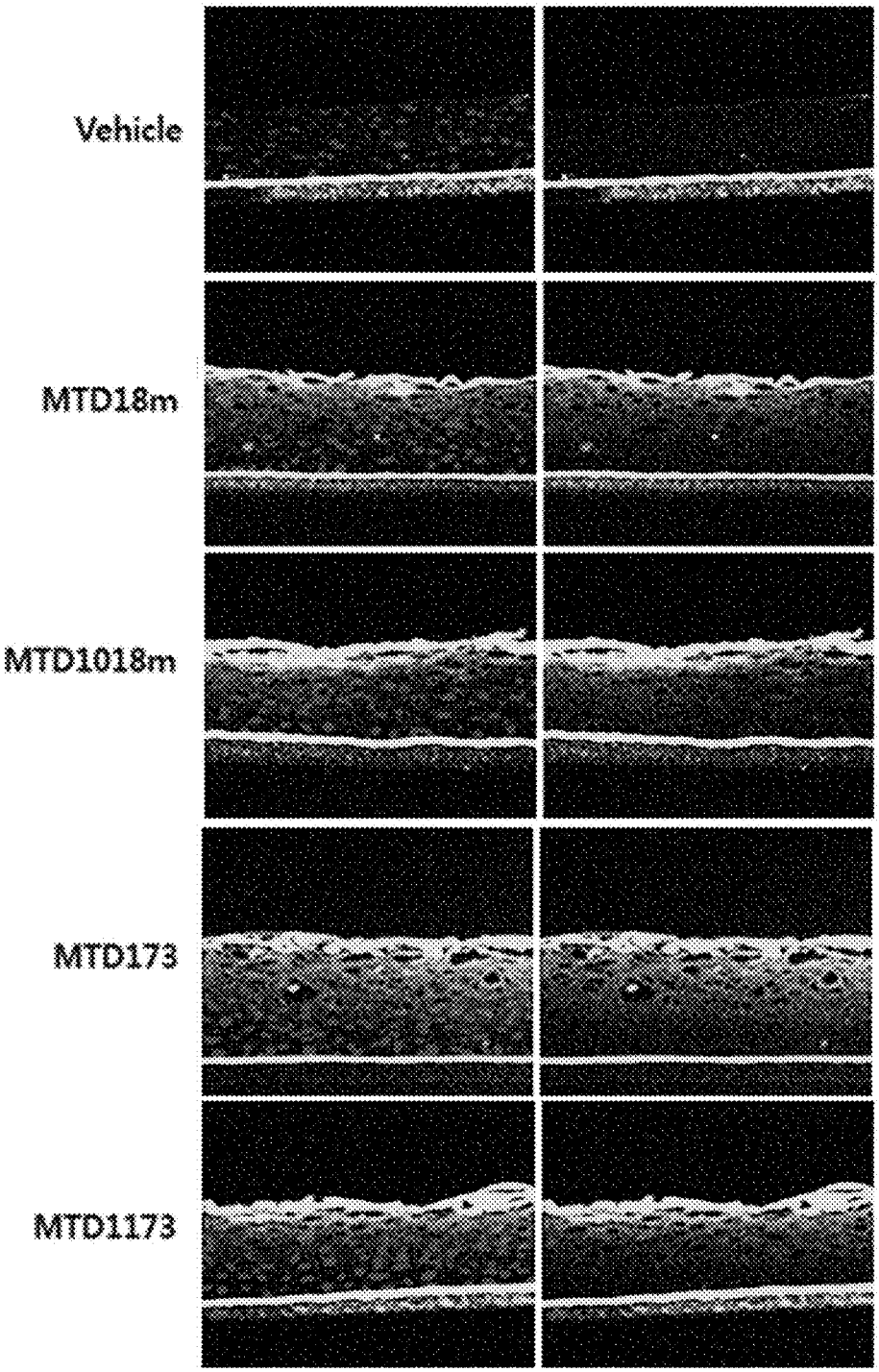
FIG. 11 shows images showing permeability in a cell tissue of a modified MTD of the present invention in EpiOral skin models, taken by confocal laser scanning microscopy.

Consequently, as shown in FIG. 11, it was confirmed that no significant level of fluorescence was shown in a negative control (vehicle), but the modified MTD used in the test was permeated into the EpiOral epithelial model according to time. In addition, compared to the conventional MTD (18m, and 173) used in the test, it was confirmed that the fluorescent material was more effectively delivered to a deep tissue, and brightness of the fluorescence was also increased in the modified MTD (1018m, and 1173A).

Example 9

Identification of In Vivo Epithelial Tissue Permeability of Modified MTD

To analyze in vivo epithelial tissue permeability of the modified MTD of the present invention, for 8-week-old female ICR mice (OrientBio, Korea), 100 µl of a fluorescent indicator (FITC)-attached modified MTD (M1067)-FITC, Tat-FITC and single FITC, each having a concentration of 100 µg was dropped on a sterilized gauze having a size of 2.5 cm×2.5 cm per individual, and fixed on a back of the mouse using Tegarderm (3M, USA). After 1, 3, 6, and 12 hours, the mice were sacrificed by cervical dislocation, and skin at the drug-applied parts was extracted. Afterward, the skin was put in 4% paraformaldehyde for 24 hours to fix a tissue and then prepared in a 6 µm cryosection to form a slide. The formed slide was treated with PBS buffer for 10 minutes to wash the fragment, and exposed to a 0.5 mM DAPI solution for 5 minutes to stain a nucleus in the tissue. The stained tissue was washed again three times with PBS buffer for 10 minutes, fixed with mounting media, and observed by confocal microscopy. The results are shown in FIG. 12.

Figure 12:
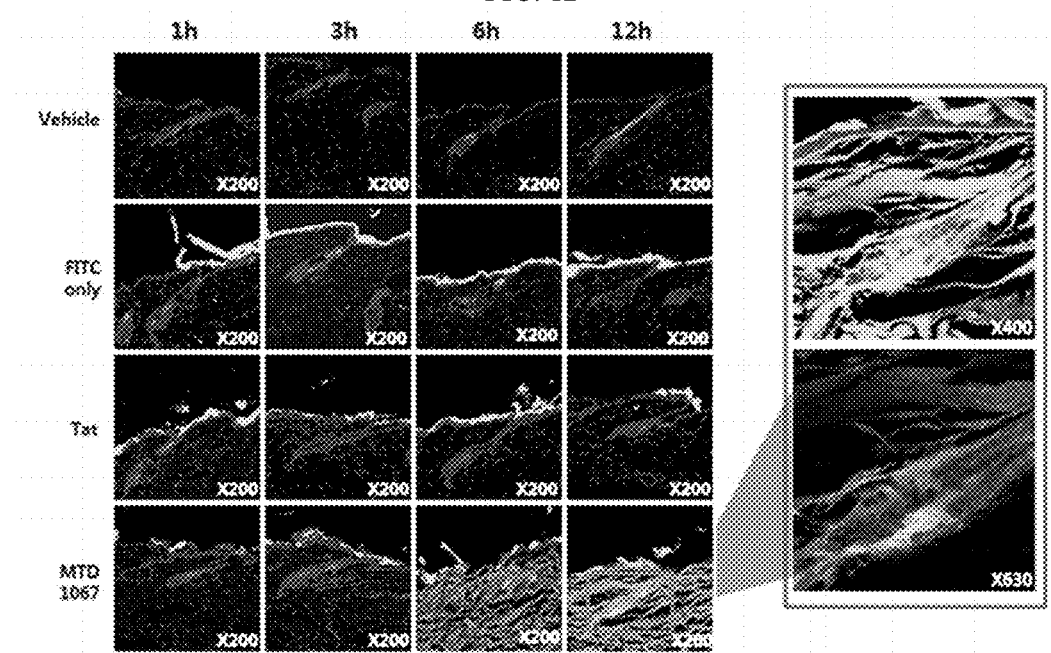
FIG. 12 is a result of identification of skin permeability of a modified MTD of the present invention in vivo through confocal laser scanning microscopy.

Consequently, as shown in FIG. 12, it was confirmed that no fluorescent signals were detected in the negative control, epithelial permeation was not induced in FITC only, and Tat-FITC treated groups since fluorescent signals were specifically detected on a stratum corneum, which is the uppermost layer of the skin. However, in the modified MTD used in the test, MTD 1067, it was confirmed that epithelial permeation into a deep tissue occurred according to applied time, and the permeated peptide was also specifically present in the cytoplasm of a skin follicular cell. Therefore, it was confirmed that the modified MTD of the present invention exhibited considerably excellent tissue permeability in vivo, as well as in vitro.

Example 10

Identification of In Vitro Cell Permeability of Peptide Complex Prepared by Linking Acetyl Hexapeptide to Modified MTD To compare cell permeability according to orientation and cargo combination of the modified MTD of the present invention, a peptide complex to which a low-molecular-weight peptide, acetyl hexapeptide, was linked was synthesized, and a test for in vitro cell permeability for the peptide complex was performed.

Particularly, to confirm the cell permeability, human skin-derived melanoma cells (A375SM, human melanoma, KCLB No. 80004, KCLB, Korea) were used, acetyl hexapeptide (AH, a peptide composed of 6 amino acids effective in enhancing wrinkles and preventing aging) was applied as the low-molecular-weight peptide, and an M1067 peptide having an amino acid sequence of SEQ. ID. NO: 16 and an M1103 peptide having an amino acid sequence of SEQ. ID. NO: 17 were used as modified MTDs.

Particularly, one day before the test, the A375SM cells were cultured in a 12-well culture plate with a glass cover slip for 24 hours. The A375SM cells were cultured in MEM media containing 10% FBS and 1% penicillin/streptomycin (10,000 units penicillin and 10,000 µg/mL streptomycin, Invitrogen) in 5% $CO_2$ humidified atmosphere at 37° C. 5 µM of each of no MTD-linked AH and modified MTD-linked MTD-AH was treated to the A375SM cells for 6 hours. After the treatment of the peptide, to observe cell permeability of the test material, the cells were fixed with 4% PFA at room temperature for 20 minutes.

To directly detect internalized MTD-AH, the cells were washed three times with phosphoric acid buffer, and counter-stained with 5 µM of 4',6-diamidino-2-phenylindole (DAPI), which is a nucleus fluorescent dye. After 10-minute DAPI staining, the cells were washed three times with phosphoric acid buffer, and counter-stained again with 5 μg/ml Con A (Concanavalin A), which is a dye for a cell membrane. After 10-minute Con A staining, the cells were washed three times with phosphoric acid buffer, and to conserve a fluorescent label of a protein, 20 μl of mounting media was dropped on a slide to observe the cells. Transfer into a nucleus and cell permeability were identified by staining each treated cell through DAPI and Con A staining to facilitate distinction of intracellular transfer parts. In addition, an original form of the cell was observed using a nomarski filter during confocal microscopy, and FITC fluorescence, DAPI fluorescence, and Con A fluorescence were observed using a filter suitable for a fluorochrome.

Figure 13:
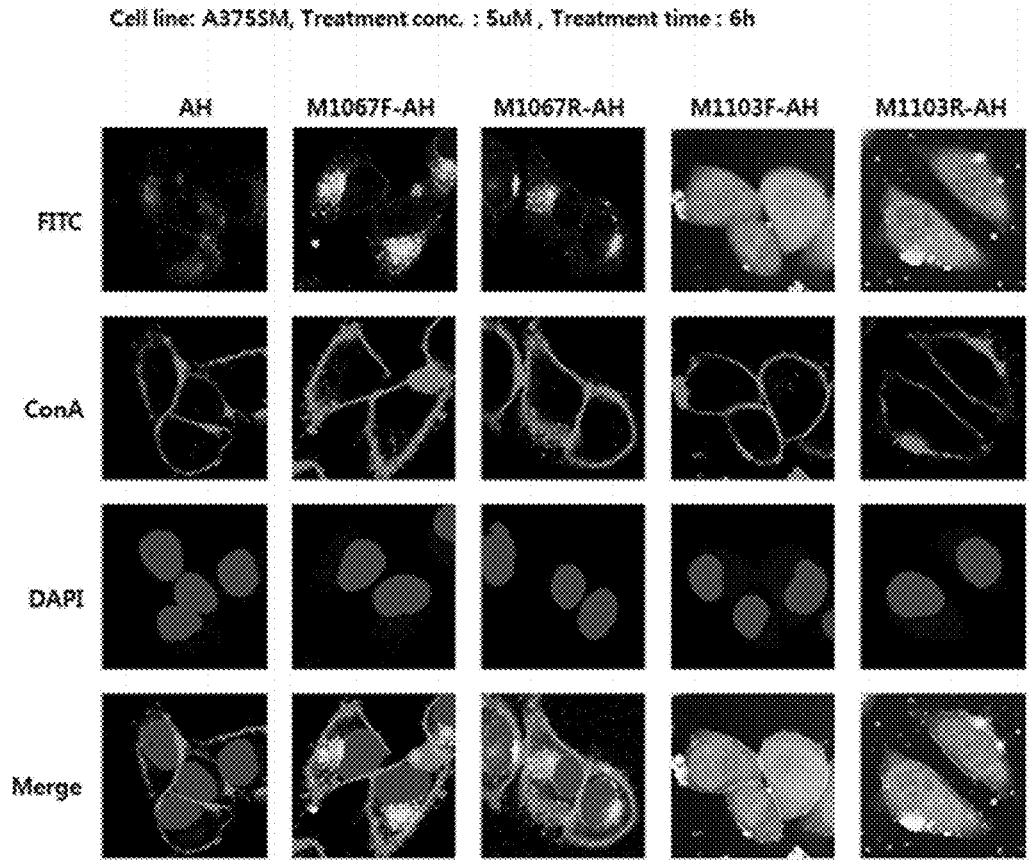
FIG. 13 is a result of identification in vitro cell permeability of a peptide complex prepared by coupling an acetyl hexapeptide with a modified MTD of the present invention through confocal laser scanning microscopy.
Figure 14:
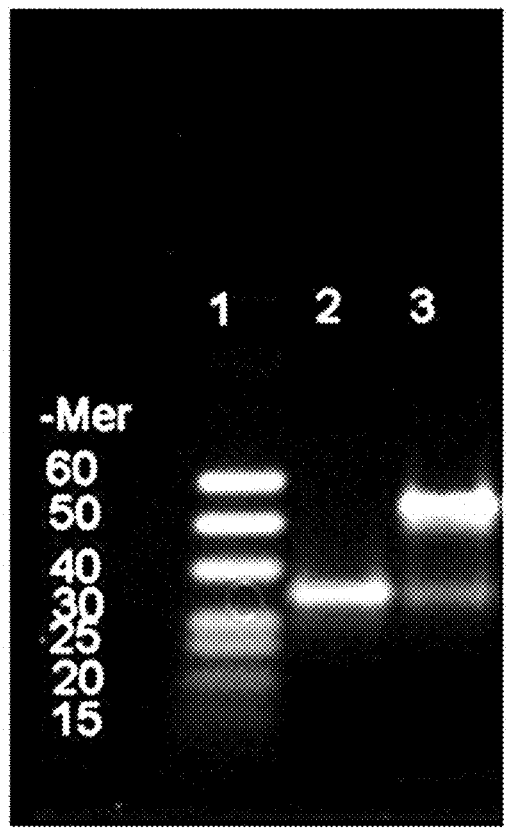
FIG. 14 is an image showing that a modified MTD is linked with LacZ siRNA by a covalent bond.

Consequently, as shown in FIG. 13, it was confirmed that M1067F-AH prepared by linking the modified MTD, M1067, to acetyl hexapeptide in a forward direction, and M1067R-AH prepared by linking the modified MTD to a c-term of acetyl hexapeptide in an inverse direction, M1103F-AH prepared by linking an amino acid of the modified MTD, M1103, to acetyl hexapeptide in a forward direction and M1103R-AH linked to a c-term of the acetyl hexapeptide in an inverse direction had considerably excellent cell permeability, compared to the acetyl hexapeptide control to which MTD was not linked.

Accordingly, it was seen that the modified MTD invented for the present invention was attached to a biologically active molecule, thereby exhibiting excellent cell permeability when the amino acid sequence of the modified MTD was linked in the forward direction, or attached while being arranged in a reverse direction, and thus the present invention is not limited in a linking direction thereof.

Example 11

Identification of In Vivo Lung Tissue Permeability of Modified MTD 11-1. Preparation of siRNA-Conjugated MTD To analyze in vivo lung tissue permeability of the modified MTD of the present invention, siRNA-conjugated MTD was primarily prepared. Here, a covalent bond between a peptide and siRNA was performed using 4FB-siRNA and HyNic-peptide according to an oligonucleotide/peptide conjugation method of solulink.

Particularly, first, N-succinimidyl-4-formylbenzamide (S-4FB) was dissolved in a DMF solution, S-4FB was input to conjugation buffer (100 mM sodium phosphate, 150 mM sodium chloride, pH 6.0) in an amount 20 times the concentrations of LacZ siRNA and LacZ siRNA, and a reaction was performed at room temperature for 2 hours. To exchange excess S-4FB present in the reaction mixture with a buffer, desalting purification was performed.

Second, succinimidyl-6-hydrazino-nicotinamide (6-Boc-Hynic) and O-Benzotriazol-1-yl-tetramethyluroniume (HBTU) were dissolved in DMF, diisopropylethylamine (Di-PEA) was added, and the resulting product was immediately added to a Fmoc-protected peptide resin. After a 1-hour reaction, for isolation from a Hynic-peptide resin, TFA/TIS/acetone/$H_2O$ (92.5/2.5/2.5/2.5) was used. The resulting product was purified by HPLC, and a Hynic-peptide was prepared through MS identification.

Third, the 4FB-modified LacZ siRNA and hynic-peptide corresponding to 5 times the molar ratio of the 4FB-modified LacZ siRNA were mixed in TurboLink Catalyst Buffer (10 mM Phosphate, 15 mM Sodium Chloride, 10 mM aniline, pH 6.0), and reacted at room temperature for 2 hours.

Finally, excess peptides were removed from the reaction product using Sartorius Vivaspin diafiltration and identified with a 2% NuSieve GTG agarose gel. A molecular weight of the peptide was identified using a mass spectrometer, and the peptide was lyophilized to prepare an siRNA-peptide covalent conjugate.

11-2. Identification of In Vivo Lung Tissue Permeability of Modified MTD

Figure 15:
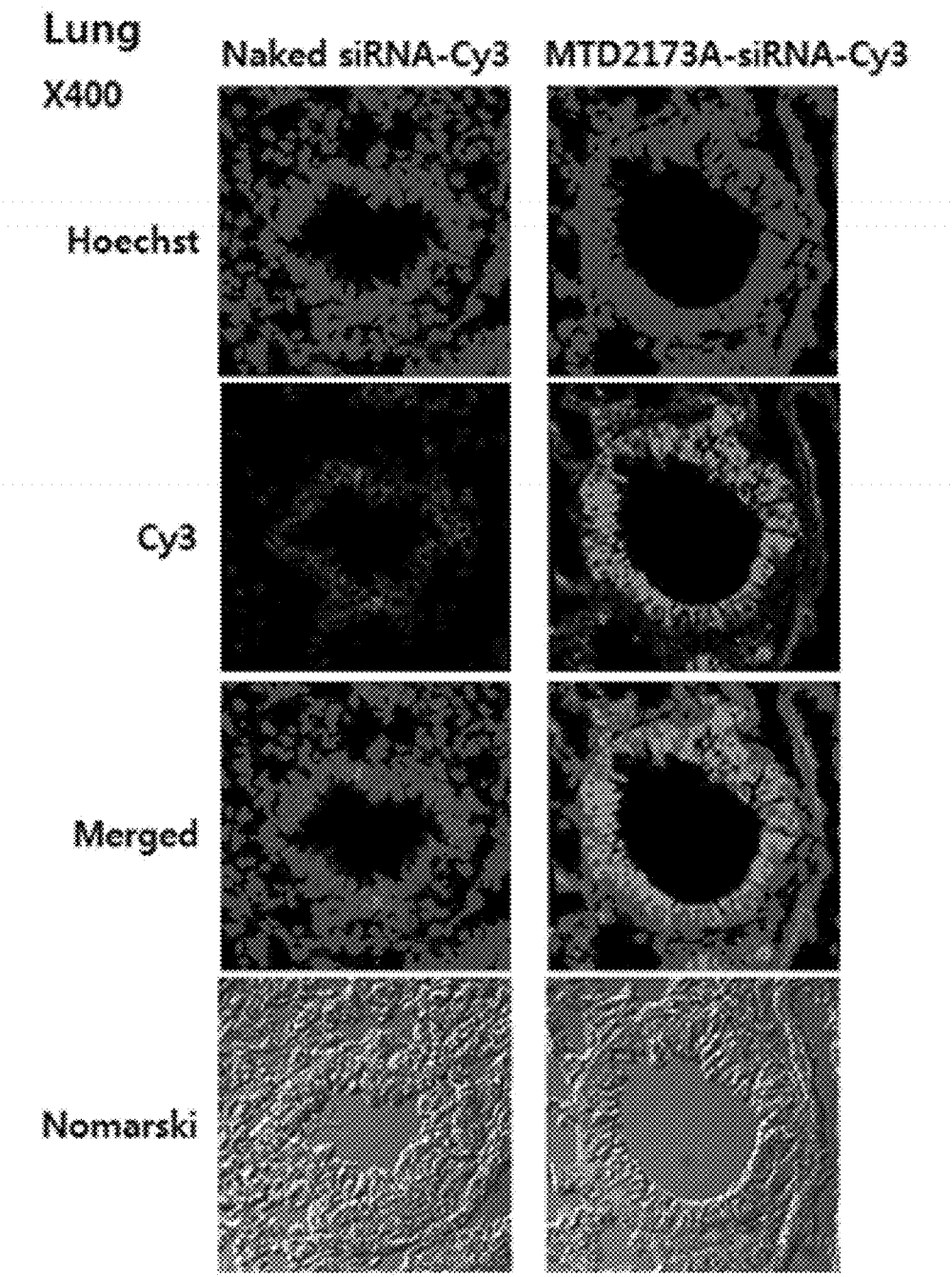
FIG. 15 shows images showing permeability into a lung tissue in a living organ of a modified MTD of the present invention intravenously injected into a mouse, taken by confocal laser scanning microscopy.

To analyze in vivo tissue permeability of the modified MTD of the present invention, 200 μg/head LacZ-siRNA-Cy3 fused to the modified MTD 2173A prepared by the method of Example 10-1 was intravenously administered into B6 ROSA26 mice continuously expressing a β-galactosidase for 3 days, and after two days, the mice were sacrificed to extract lungs. The extracted lungs were put into 4% paraformaldehyde (PFA) for 15 hours or more to be fixed, a cryosection was prepared using a Microm freezing microtome (Microm HM520 cryostat, Thermo), and put on a glass slide to manufacture a slide for microscopy. The manufactured slide was treated with phosphoric acid buffer for 10 minutes to wash a fragment, and treated with a 0.5 mM DAPI solution for 5 minutes to stain a nucleus in a tissue. The stained tissue was washed again with phosphoric acid buffer three times for 10 minutes, fixed using mounting media, and observed by confocal microscopy. The results are shown in FIG. 15. Afterward, the manufactured slide as described above was reacted in X-gal dye overnight, and then a tissue was stained with hematoxylene-eosin (HE) staining to observe activity of a β-galactosidase. The results are shown in FIG. 16.

Consequently, as shown in FIG. 15, it was seen that no significant level of fluorescence was observed in the negative control (Vehicle), but intracellular permeation of a lung tissue occurred in the MTD-LacZ siRNA-Cy3 used in the test.

Figure 16:
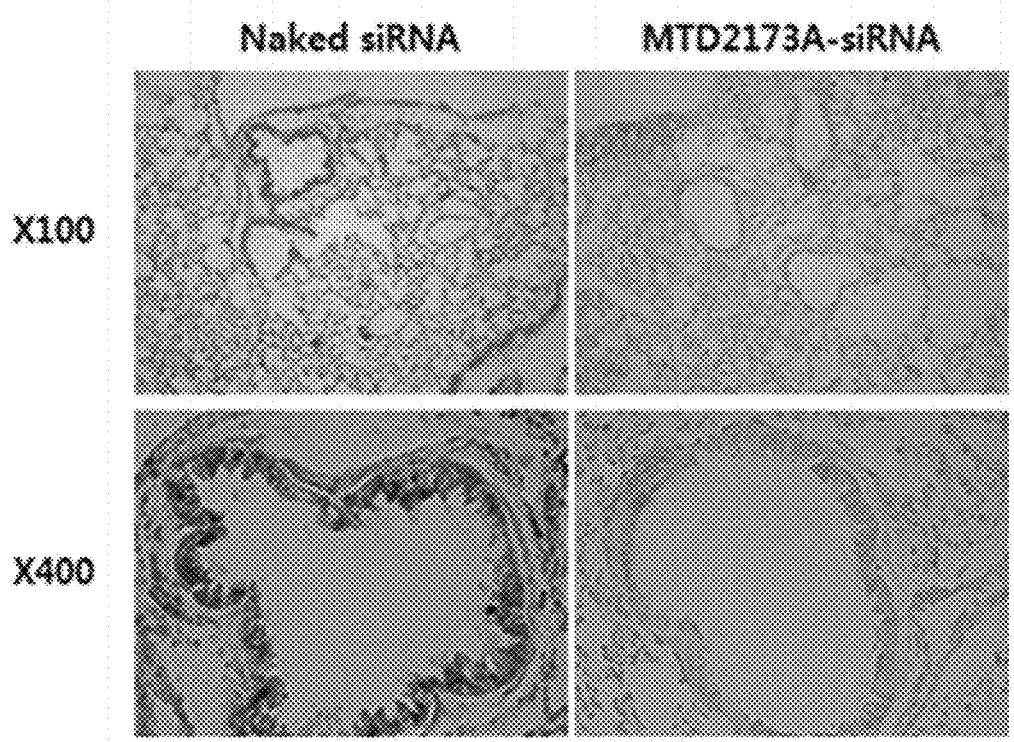
FIG. 16 shows images showing that, when a modified MTD is intravenously injected into a mouse, the modified MTD is permeated into a lung tissue in a living body, thereby reducing expression of β-galactosidase proteins.

In addition, as shown in FIG. 16, it was seen that the β-galactosidase activity was observed in most of organ fragments in the negative control, but rarely observed in an organ fragment of MTD-LacZ siRNA-Cy3-injected mice.

Accordingly, it can be seen that the modified MTD of the present invention may be used in delivery of a material such as siRNA or a drug, which is difficult to deliver into cells, and may effectively deliver the material or drug into an organ tissue, and the delivered material or drug can be effective in the tissue.

Therefore, it was seen that the modified MTD of the present invention was also enhanced in in vivo permeability into a tissue, as well as intracellular permeability, compared to the conventional MTD.

Example 12

Evaluation of Skin Safety of Modified MTD to which a Dermatological Active Substance was Coupled 12-1. Synthesis of Modified MTD-Coumaric Acid A 20% piperidine/N-methylpyrrolidone solution was treated to the modified MTD (M1067) synthesized in Example 4, in which the amino acid at the N-terminus was coupled, to remove an Fmoc group, washed with N-methylpyrrolidone and dichloromethane, and a commercially available compound, coumaric acid (Sigma, USA), was coupled thereto. After the coupling, the resulting product was washed with N-methylpyrrolidone and dichloromethane several times, and dried under nitrogen gas. Here, the dried product was treated with a solution containing trifluoroacetic acid:phenol:thioanisole:water:triisopropylsilane in a ratio of 90:2.5:2.5:2.5:2.5 (v/v) for 2 to 3 hours to remove a peptide protecting group, the peptide-linked coumaric acid was isolated from a resin, and the peptide was precipitated with diethylether. 10% Pd/C was added to methanol to remove a benzyl group protecting an alcohol group binding to the 9th carbon of C of the coumaric acid and stirred at room temperature for approximately 1 hour under hydrogen, and a remaining solution obtained by removing the Pd/C using celite was decompressed and concentrated. The modified MTD-coumaric acid derivative obtained as described above was purified using purified reverse phase high performance liquid chromatography column (Zobax, C8 300 Å, 21.1 mm×25 cm) with a gradient of acetonitrile containing 0.1% trifluoroacetic acid, thereby synthesizing a modified MTD-coumaric acid derivative in which coumaric acid was coupled to a modified MTD having an amino acid sequence of SEQ. ID. NO: 16 represented by Formula 2.

[Formula 2]
(4-Hydroxycinnamoyl) Ala Ala Val Ala Pro Ala Ala

Ala Arg Met

12-2. Synthesis of Modified MTD-Acetyl Pentapeptide

Acetyl pentapeptides (acetylated Lys Ther Ther Lys Ser), which are peptides commercially available in the cosmetics industry, were sequentially synthesized on the modified MTD (M1067) having the amino acid sequence of SEQ. ID. NO: 16 synthesized in Example 4, in which the amino acid at the N-terminus was coupled, treated with a 20% piperidine/N-methylpyrrolidone solution to remove an Fmoc group, washed with N-methylpyrrolidone and dichloromethane several times, and dried under nitrogen gas. Here, the dried product was treated with a solution containing trifluoroacetic acid:phenol:thioanisole:water:triisopropylsilane in a ratio of 90:2.5:2.5:2.5:2.5 (v/v) for 2 to 3 hours to remove a peptide protecting group, and the peptide was isolated from a resin, and then precipitated with diethylether. The modified MTD-acetyl pentapeptide derivative obtained as described above was purified using a purified reverse phase high performance liquid chromatography column (Zobax, C8 300 Å, 21.1 mm×25 cm) with a gradient of acetonitrile containing 0.1% trifluoroacetic acid, thereby synthesizing a modified MTD (M1067) having the amino acid sequence of SEQ. ID. NO: 16, which was represented by Formula 3.

[Formula 3]
Met Arg Ala Ala Ala Pro Ala Val Ala Ala Lys*

Ther Ther Lys Ser

*: acetylated lysine

12-3. Preparation of Composition for Cosmetic Containing Modified MTD (M1067)-Coumaric Acid An essence composition containing modified MTD (M1067)-coumaric acid or modified MTD (M1067) was formulated in a composition shown in Table 1 as follows.

Components 1 to 6 were added to a water dissolver, heated to 70° C. to completely dissolve, and transferred to an emulsifying tank. Components 7 to 11 were added to an oil dissolver, heated to 70° C. to completely dissolve, and mixed in the emulsifying tank. The contents were cooled to 40° C., and components 12, 13 and 15 were added to the emulsifying tank, and cooled to room temperature, thereby preparing a composition containing modified MTD (M1067)—coumaric acid.

Comparative Example 1

Components 1 to 6 were added to a water dissolver, heated to 70° C. to completely dissolve, and transferred to an emulsifying tank. Components 7 to 11 were added to an oil dissolver, heated to 70° C. to completely dissolve, and mixed in the emulsifying tank. The contents were cooled to 40° C., and components 12 to 14 were added to the emulsifying tank, and cooled to room temperature, thereby preparing a composition containing modified MTD (M1067).

Comparative Example 2

Components 1 to 6 were added to a water dissolver, heated to 70° C. to completely dissolve, and transferred to an emulsifying tank. Components 7 to 11 and 16 were added to an oil dissolver, heated to 70° C. to completely dissolve, and mixed in the emulsifying tank. The contents were cooled to 40° C., and components 12 and 13 were added to the emulsifying tank, and cooled at a room temperature, thereby preparing a composition containing coumaric acid.

TABLE 1

Composition of essence composition containing a modified MTD (M1067)-coumaric acid (unit: wt %)

| No | Component | Example 12-1 | Comparative Example 1 | Comparative Example 2 |
|---|---|---|---|---|
| 1 | Distilled water | 84.480 | 84.480 | 64.480 |
| 2 | Alcohol | 0.000 | 0.000 | 20.000 |
| 3 | Glycerin | 5.000 | 5.000 | 5.000 |
| 4 | Dipropylene glycol | 3.000 | 3.000 | 3.000 |
| 5 | Allatoin | 0.100 | 0.100 | 0.100 |
| 6 | Disodium EDTA | 0.020 | 0.020 | 0.020 |
| 7 | Olive oil | 2.000 | 2.000 | 2.000 |
| 8 | Caprylic/capric triglyceride | 2.000 | 2.000 | 2.000 |
| 9 | Sodium acrylate/ sodium acrylodimethyl taurate copolymer | 0.667 | 0.667 | 0.667 |
| 10 | Isohexadecane | 0.667 | 0.667 | 0.667 |
| 11 | Polysorbate 80 | 0.667 | 0.667 | 0.667 |
| 12 | Chlorophenesin | 0.250 | 0.250 | 0.250 |
| 13 | Methylparaben | 0.150 | 0.150 | 0.150 |
| 14 | Intracellular molecular transduction peptide | 0.000 | 1.000 | 0.000 |
| 15 | Intracellular molecular transduction peptide-coumaric acid | 1.000 | 0.000 | 0.000 |
| 16 | Coumaric acid | 0.000 | 0.000 | 1.000 |

12-4. Preparation of Cosmetic Composition Containing Modified MTD (M1067)-Acetyl Pentapeptide An essence composition containing modified MTD (M1067)-acetyl pentapeptide or modified MTD (M1067) was formulated in the composition shown in Table 2 as follows.

Components 1 to 5 were added to a water dissolver, heated to 70° C. to completely dissolve, and transferred to an emulsifying tank. Components 6 to 10 were added to an oil dissolver, heated to 70° C. to completely dissolve, and mixed in the emulsifying tank. The contents were cooled to 40° C., and components 11, 12 and 14 were added to the emulsifying tank, and cooled to room temperature, thereby preparing a composition containing modified MTD (M1067)-acetyl pentapeptide.

Comparative Example 3

Components 1 to 5 were added to a water dissolver, heated to 70° C. to completely dissolve, and transferred to an emulsifying tank. Components 6 to 10 were added to an oil dissolver, heated to 70° C. to completely dissolve, and mixed in the emulsifying tank. The contents were cooled to 40° C., and components 11 to 13 were added to the emulsifying tank, and cooled to room temperature, thereby preparing a composition containing modified MTD (M1067).

Comparative Example 4

Components 1 to 5 were added to a water dissolver, heated to 70° C. to completely dissolve, and transferred to an emulsifying tank. Components 7 to 11 and 16 were added to an oil dissolver, heated to 70° C. to completely dissolve, and mixed in the emulsifying tank. The contents were cooled to 40° C., and components 11, 12 and 15 were added to the emulsifying tank, and cooled to room temperature, thereby preparing a composition containing coumaric acid.

TABLE 2

Essence composition containing modified MTD (M1067)-acetyl pentapeptide (unit: wt %)

| No | Component | Comparative Example 12-2 | Comparative Example 3 | Comparative Example 4 |
|---|---|---|---|---|
| 1 | Distilled water | Up to 100 | Up to 100 | Up to 100 |
| 2 | Glycerin | 5.000 | 5.000 | 5.000 |
| 3 | Dipropylene glycol | 3.000 | 3.000 | 3.000 |
| 4 | Allatoin | 0.100 | 0.100 | 0.100 |
| 5 | Disodium EDTA | 0.020 | 0.020 | 0.020 |
| 6 | Olive oil | 2.000 | 2.000 | 2.000 |
| 7 | Caprylic/capric triglyceride | 2.000 | 2.000 | 2.000 |
| 8 | Sodium acrylate/ sodium acrylodimethyl taurate copolymer | 0.667 | 0.667 | 0.667 |
| 9 | Isohexadecane | 0.667 | 0.667 | 0.667 |
| 10 | Polysorbate 80 | 0.667 | 0.667 | 0.667 |
| 11 | Chlorophenesin | 0.250 | 0.250 | 0.250 |
| 12 | Methylparaben | 0.150 | 0.150 | 0.150 |

TABLE 2-continued

Essence composition containing modified MTD (M1067)-acetyl pentapeptide (unit: wt %)

| No | Component | Comparative Example 12-2 | Comparative Example 3 | Comparative Example 4 |
|---|---|---|---|---|
| 13 | Intracellular molecular transduction peptide | 0.000 | 0.100 | 0.000 |
| 14 | Intracellular molecular transduction peptide - acetyl pentapeptide | 0.100 | 0.000 | 0.000 |
| 15 | Acetyl pentapeptide | 0.000 | 0.000 | 0.100 |

12-5. Evaluation of Skin Safety of Complex of Modified MTD and a Dermatological Active Substance To confirm safety of the modified MTD (M1067) synthesized in Example 4, the modified MTD (M1067)-coumaric acid and the modified MTD (M1067)-acetyl pentapeptide synthesized in Examples 12-1 and 12-2, a primary stimulus test using human skin was performed. The test was conducted by a specialized clinical research organization, Dermapro, and the clinical composition was prepared as will be described below. 30 or more subjects meeting standards for the clinical test and not falling under exclusion standards were selected. Sample materials were applied to backs of the subjects, and removed after 48 hours. The test sites were observed 30 minutes and 24 hours later, after the removal.

The skin evaluation was performed by the Frosch & Kligman method (Frosch P. J and Kligman A. M. J Am Acad Dermatol, 1(1):35-41 (1979)) and standards shown in Table 3 reflecting the Cosmetic, Toiletry, and Fragrance Association (CTFA) guidelines (The Cosmetic, Toiletry and Fragrance Association, Inc. Washington, D.C. 20005 (1981)), average degrees of reaction after 48 and 72 hours were compared, and results were determined based on the average degree of reaction of each composition.

TABLE 3

Recording of patch test reactions

| Symbol | Grade | Clinical Description |
|---|---|---|
| + | 1 | Slight erythema, either spotty or diffuse |
| ++ | 2 | Moderate uniform erythema |
| +++ | 3 | Intense erythema with edema |
| ++++ | 4 | Intense erythema with edema & vesicles |

TABLE 4

Results of primary stimulus test for human skin (n = 30)

| No. | Name of test material | No. of responder | 48 hrs 1+ | 2+ | 3+ | 72 hrs 1+ | 2+ | 3+ | 47 h | 72 h | Mean |
|---|---|---|---|---|---|---|---|---|---|---|---|
| 1 | Containing 0.1% modified MTD (M1067) | 0 | — | — | — | — | — | — | 0.0 | 0.0 | 0.0 |
| 2 | Containing 1% modified MTD (M1067) | 0 | — | — | — | — | — | — | 0.0 | 0.0 | 0.0 |
| 3 | Containing 1% modified MTD (M1067)-coumaric acid | 0 | — | — | — | — | — | — | 0.0 | 0.0 | 0.0 |
| 4 | Containing 1% coumaric acid | 0 | — | — | — | — | — | — | 0.0 | 0.0 | 0.0 |
| 5 | Containing 0.1% modified MTD (M1067)-acetyl pentapeptide | 0 | — | — | — | — | — | — | 0.0 | 0.0 | 0.0 |
| 6 | Containing 0.1% acetyl pentapeptide | 0 | — | — | — | — | — | — | 0.0 | 0.0 | 0.0 |
| 7 | Control (Squalane) | 0 | — | — | — | — | — | — | 0.0 | 0.0 | 0.0 |

As shown in Table 4, the modified MTD (M1067), the modified MTD (M1067)-coumaric acid and the modified MTD (M1067)-acetyl pentapeptide were evaluated as low-stimuli materials in the human skin primary stimulus test. Accordingly, it was proved that the modified MTD (M1067) can be used safely on humans through the clinical test conducted by the specialized research organization.

In addition, it can be seen that the modified MTD of the present invention was also improved in intracellular permeability and in vivo permeability in a tissue more than the conventional MTD through the above-described Examples.

Moreover, the modified MTD was also proved to be safe for humans, and thus can be effectively used in various researches, and treatment of a patient of a specific disease required for effective drug delivery, resulting in high usefulness in development of new and modified drugs.

While the invention has been shown and described with reference to certain exemplary embodiments thereof, it will be understood by those skilled in the art that various changes in form and details may be made therein without departing from the scope of the invention as defined by the appended claims.

The invention claimed is:

1. A peptide comprising an amino acid sequence selected from the group consisting of SEQ ID NOs: 15 and 17-35.

2. A peptide consisting of an amino acid sequence selected from the group consisting of SEQ ID NOs: 15 to 35, wherein the peptide mediates transport of a biologically active molecule into a cell.

3. A method of genetically engineering a conjugate, wherein the conjugate comprises a biologically active molecule conjugated to a peptide comprising an amino acid sequence selected from the group consisting of SEQ ID NOs: 15-35, comprising: attaching the peptide to the biologically active molecule.

4. A method for transporting a biologically active molecule into a cell of an individual, comprising: administering a conjugate, wherein the conjugate comprises a biologically active molecule conjugated to a peptide comprising an amino acid sequence selected from the group consisting of SEQ ID NOs: 15-35, to the individual.

* * * * *

SEQUENCE LISTING

```
<160> NUMBER OF SEQ ID NOS: 61

<210> SEQ ID NO 1
<211> LENGTH: 14
<212> TYPE: PRT
<213> ORGANISM: Artificial Sequence
<220> FEATURE:
<223> OTHER INFORMATION: MTD JO-018 amino acid sequence

<400> SEQUENCE: 1

Ala Ala Leu Ile Gly Ala Val Leu Ala Pro Val Val Ala Val
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: MTD JO-067 Amino Acid sequence

<400> SEQUENCE: 2

Ala Ala Ala Pro Ala Val Ala Ala
 1               5

<210> SEQ ID NO 3
<211> LENGTH: 9
<212> TYPE: PRT
<213> ORGANISM: Artificial Sequence
<220> FEATURE:
<223> OTHER INFORMATION: MTD JO-103 Amino Acid sequence

<400> SEQUENCE: 3

Leu Ala Leu Pro Val Leu Leu Leu Ala
 1               5

<210> SEQ ID NO 4
<211> LENGTH: 12
<212> TYPE: PRT
<213> ORGANISM: Artificial Sequence
<220> FEATURE:
<223> OTHER INFORMATION: MTD JO-159 Amino Acid sequence

<400> SEQUENCE: 4

Ile Ala Ile Ala Ala Ile Pro Ala Ile Leu Ala Leu
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: MTD JO-173 Amino Acid sequence

<400> SEQUENCE: 5
```

Ala Val Ile Pro Ile Leu Ala Val Pro
 1               5

<210> SEQ ID NO 6
<211> LENGTH: 14
<212> TYPE: PRT
<213> ORGANISM: Artificial Sequence
<220> FEATURE:
<223> OTHER INFORMATION: MTD 18m Amino Acid Sequence

<400> SEQUENCE: 6

Pro Ala Ala Leu Ala Ala Leu Pro Val Ala Val Val Ala Val
 1               5                   10

<210> SEQ ID NO 7
<211> LENGTH: 9
<212> TYPE: PRT
<213> ORGANISM: Artificial Sequence
<220> FEATURE:
<223> OTHER INFORMATION: MTD 173A Amino Acid Sequence

<400> SEQUENCE: 7

Pro Ala Val Ile Pro Ile Leu Ala Val
 1               5

<210> SEQ ID NO 8
<211> LENGTH: 42
<212> TYPE: DNA
<213> ORGANISM: Artificial Sequence
<220> FEATURE:
<223> OTHER INFORMATION: MTD JO-018 polynucleotide Sequence

<400> SEQUENCE: 8
gcggcgctga ttggcgcggt gctggcgccg gtggtggcgg tg                          42

<210> SEQ ID NO 9
<211> LENGTH: 24
<212> TYPE: DNA
<213> ORGANISM: Artificial Sequence
<220> FEATURE:
<223> OTHER INFORMATION: MTD JO-067 polynucleotide Sequence

<400> SEQUENCE: 9
gcggcggcgc cggcggtggc ggcg                                              24

<210> SEQ ID NO 10
<211> LENGTH: 27
<212> TYPE: DNA
<213> ORGANISM: Artificial Sequence
<220> FEATURE:
<223> OTHER INFORMATION: MTD JO-103 polynucleotide Sequence

<400> SEQUENCE: 10
ctggcgctgc cggtgctgct gctggcg                                           27

<210> SEQ ID NO 11
<211> LENGTH: 36
<212> TYPE: DNA
<213> ORGANISM: Artificial Sequence
<220> FEATURE:
<223> OTHER INFORMATION: MTD JO-159 polynucleotide Sequence

<400> SEQUENCE: 11
aatgcgaatg cggcgaatcc ggcgaatctg gcgctg                                 36

<210> SEQ ID NO 12

<210> SEQ ID NO 12
<211> LENGTH: 27
<212> TYPE: DNA
<213> ORGANISM: Artificial Sequence
<220> FEATURE:
<223> OTHER INFORMATION: MTD JO-173 polynucleotide Sequence

<400> SEQUENCE: 12
gcggtgaatc cgaatctggc ggtgccg                                    27

<210> SEQ ID NO 13
<211> LENGTH: 42
<212> TYPE: DNA
<213> ORGANISM: Artificial Sequence
<220> FEATURE:
<223> OTHER INFORMATION: MTD JO-018m polynucleotide Sequence

<400> SEQUENCE: 13
ccggcggcgc tggcggcgct gccggtggcg gtggtggcgg tg                   42

<210> SEQ ID NO 14
<211> LENGTH: 27
<212> TYPE: DNA
<213> ORGANISM: Artificial Sequence
<220> FEATURE:
<223> OTHER INFORMATION: MTD JO-173A polynucleotide Sequence

<400> SEQUENCE: 14
ccggcggtga atccgaatct ggcggtg                                    27

<210> SEQ ID NO 15
<211> LENGTH: 16
<212> TYPE: PRT
<213> ORGANISM: Artificial Sequence
<220> FEATURE:
<223> OTHER INFORMATION: MTD 1018 Amino Acid Sequence

<400> SEQUENCE: 15

Met Arg Ala Ala Leu Ile Gly Ala Val Leu Ala Pro Val Val Ala Val
 1               5                  10                  15

<210> SEQ ID NO 16
<211> LENGTH: 10
<212> TYPE: PRT
<213> ORGANISM: Artificial Sequence
<220> FEATURE:
<223> OTHER INFORMATION: MTD 1067 Amino Acid Sequence

<400> SEQUENCE: 16

Met Arg Ala Ala Ala Pro Ala Val Ala Ala
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: MTD 1103 Amino Acid Sequence

<400> SEQUENCE: 17

Met Arg Leu Ala Leu Pro Val Leu Leu Leu Ala
 1               5                  10

<210> SEQ ID NO 18
<211> LENGTH: 14
<212> TYPE: PRT
<213> ORGANISM: Artificial Sequence
<220> FEATURE:

```
<223> OTHER INFORMATION: MTD 1159 Amino Acid Sequence

<400> SEQUENCE: 18

Met Arg Ile Ala Ile Ala Ala Ile Pro Ala Ile Leu Ala Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: MTD 1173 Amino Acid Sequence

<400> SEQUENCE: 19

Met Arg Ala Val Ile Pro Ile Leu Ala Val Pro
1               5                   10

<210> SEQ ID NO 20
<211> LENGTH: 16
<212> TYPE: PRT
<213> ORGANISM: Artificial Sequence
<220> FEATURE:
<223> OTHER INFORMATION: MTD 1018m Amino Acid Sequence

<400> SEQUENCE: 20

Met Arg Pro Ala Ala Leu Ala Ala Leu Pro Val Ala Val Val Ala Val
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: MTD 1173A Amino Acid Sequence

<400> SEQUENCE: 21

Met Arg Pro Ala Val Ile Pro Ile Leu Ala Val
1               5                   10

<210> SEQ ID NO 22
<211> LENGTH: 16
<212> TYPE: PRT
<213> ORGANISM: Artificial Sequence
<220> FEATURE:
<223> OTHER INFORMATION: MTD 2018 Amino Acid Sequence

<400> SEQUENCE: 22

Met His Ala Ala Leu Ile Gly Ala Val Leu Ala Pro Val Val Ala Val
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: MTD 2067 Amino Acid Sequence

<400> SEQUENCE: 23

Met His Ala Ala Ala Pro Ala Val Ala Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: MTD 2103 Amino Acid Sequence
```

```
<400> SEQUENCE: 24

Met His Leu Ala Leu Pro Val Leu Leu Leu Ala
 1               5                  10

<210> SEQ ID NO 25
<211> LENGTH: 14
<212> TYPE: PRT
<213> ORGANISM: Artificial Sequence
<220> FEATURE:
<223> OTHER INFORMATION: MTD 2159 Amino Acid Sequence

<400> SEQUENCE: 25

Met His Ile Ala Ile Ala Ala Ile Pro Ala Ile Leu Ala Leu
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: MTD 2173 Amino Acid Sequence

<400> SEQUENCE: 26

Met His Ala Val Ile Pro Ile Leu Ala Val Pro
 1               5                  10

<210> SEQ ID NO 27
<211> LENGTH: 16
<212> TYPE: PRT
<213> ORGANISM: Artificial Sequence
<220> FEATURE:
<223> OTHER INFORMATION: MTD 2018m Amino Acid Sequence

<400> SEQUENCE: 27

Met His Pro Ala Ala Leu Ala Ala Leu Pro Val Ala Val Val Ala Val
 1               5                  10                  15

<210> SEQ ID NO 28
<211> LENGTH: 11
<212> TYPE: PRT
<213> ORGANISM: Artificial Sequence
<220> FEATURE:
<223> OTHER INFORMATION: MTD 2173A Amino Acid Sequence

<400> SEQUENCE: 28

Met His Pro Ala Val Ile Pro Ile Leu Ala Val
 1               5                  10

<210> SEQ ID NO 29
<211> LENGTH: 16
<212> TYPE: PRT
<213> ORGANISM: Artificial Sequence
<220> FEATURE:
<223> OTHER INFORMATION: MTD 3018 Amino Acid Sequence

<400> SEQUENCE: 29

Met Lys Ala Ala Leu Ile Gly Ala Val Leu Ala Pro Val Val Ala Val
 1               5                  10                  15

<210> SEQ ID NO 30
<211> LENGTH: 10
<212> TYPE: PRT
<213> ORGANISM: Artificial Sequence
<220> FEATURE:
<223> OTHER INFORMATION: MTD 3067 Amino Acid Sequence
```

```
<400> SEQUENCE: 30

Met Lys Ala Ala Ala Pro Ala Val Ala Ala
 1               5                   10

<210> SEQ ID NO 31
<211> LENGTH: 11
<212> TYPE: PRT
<213> ORGANISM: Artificial Sequence
<220> FEATURE:
<223> OTHER INFORMATION: MTD 3103 Amino Acid Sequence

<400> SEQUENCE: 31

Met Lys Leu Ala Leu Pro Val Leu Leu Leu Ala
 1               5                   10

<210> SEQ ID NO 32
<211> LENGTH: 14
<212> TYPE: PRT
<213> ORGANISM: Artificial Sequence
<220> FEATURE:
<223> OTHER INFORMATION: MTD 3159 Amino Acid Sequence

<400> SEQUENCE: 32

Met Lys Ile Ala Ile Ala Ala Ile Pro Ala Ile Leu Ala Leu
 1               5                   10

<210> SEQ ID NO 33
<211> LENGTH: 11
<212> TYPE: PRT
<213> ORGANISM: Artificial Sequence
<220> FEATURE:
<223> OTHER INFORMATION: MTD 3173 Amino Acid Sequence

<400> SEQUENCE: 33

Met Lys Ala Val Ile Pro Ile Leu Ala Val Pro
 1               5                   10

<210> SEQ ID NO 34
<211> LENGTH: 16
<212> TYPE: PRT
<213> ORGANISM: Artificial Sequence
<220> FEATURE:
<223> OTHER INFORMATION: MTD 3018m Amino Acid Sequence

<400> SEQUENCE: 34

Met Lys Pro Ala Ala Leu Ala Ala Leu Pro Val Ala Val Val Ala Val
 1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: MTD 3173A Amino Acid Sequence

<400> SEQUENCE: 35

Met Lys Pro Ala Val Ile Pro Ile Leu Ala Val
 1               5                   10

<210> SEQ ID NO 36
<211> LENGTH: 48
<212> TYPE: DNA
<213> ORGANISM: Artificial Sequence
<220> FEATURE:
<223> OTHER INFORMATION: MTD 1018 polynucleotide sequence

<400> SEQUENCE: 36
```

```
atgagggcgg cgctgattgg cgcggtgctg gcgccggtgg tggcggtg          48
```

<210> SEQ ID NO 37
<211> LENGTH: 30
<212> TYPE: DNA
<213> ORGANISM: Artificial Sequence
<220> FEATURE:
<223> OTHER INFORMATION: MTD 1067 polynucleotide Sequence

<400> SEQUENCE: 37

```
atgagggcgg cggcgccggc ggtggcggcg                              30
```

<210> SEQ ID NO 38
<211> LENGTH: 33
<212> TYPE: DNA
<213> ORGANISM: Artificial Sequence
<220> FEATURE:
<223> OTHER INFORMATION: MTD 1103 polynucleotide Sequence

<400> SEQUENCE: 38

```
atgaggctgg cgctgccggt gctgctgctg gcg                          33
```

<210> SEQ ID NO 39
<211> LENGTH: 42
<212> TYPE: DNA
<213> ORGANISM: Artificial Sequence
<220> FEATURE:
<223> OTHER INFORMATION: MTD 1159 polynucleotide Sequence

<400> SEQUENCE: 39

```
atgaggattg cgattgcggc gattccggcg attctggcgc tg                42
```

<210> SEQ ID NO 40
<211> LENGTH: 33
<212> TYPE: DNA
<213> ORGANISM: Artificial Sequence
<220> FEATURE:
<223> OTHER INFORMATION: MTD 1173 polynucleotide Sequence

<400> SEQUENCE: 40

```
atgagggcgg tgattccgat tctggcggtg ccg                          33
```

<210> SEQ ID NO 41
<211> LENGTH: 48
<212> TYPE: DNA
<213> ORGANISM: Artificial Sequence
<220> FEATURE:
<223> OTHER INFORMATION: MTD 1018m polynucleotide Sequence

<400> SEQUENCE: 41

```
atgaggccgg cggcgctggc ggcgctgccg gtggcggtgg tggcggtg          48
```

<210> SEQ ID NO 42
<211> LENGTH: 33
<212> TYPE: DNA
<213> ORGANISM: Artificial Sequence
<220> FEATURE:
<223> OTHER INFORMATION: MTD 1173A polynucleotide Sequence

<400> SEQUENCE: 42

```
atgaggccgg cggtgattcc gattctggcg gtg                          33
```

<210> SEQ ID NO 43
<211> LENGTH: 48
<212> TYPE: DNA

<213> ORGANISM: Artificial Sequence
<220> FEATURE:
<223> OTHER INFORMATION: MTD 2018 polynucleotide sequence

<400> SEQUENCE: 43
atgcacgcgg cgctgattgg cgcggtgctg gcgccggtgg tggcggtg            48

<210> SEQ ID NO 44
<211> LENGTH: 30
<212> TYPE: DNA
<213> ORGANISM: Artificial Sequence
<220> FEATURE:
<223> OTHER INFORMATION: MTD 2067 polynucleotide Sequence

<400> SEQUENCE: 44
atgcacgcgg cggcgccggc ggtggcggcg            30

<210> SEQ ID NO 45
<211> LENGTH: 33
<212> TYPE: DNA
<213> ORGANISM: Artificial Sequence
<220> FEATURE:
<223> OTHER INFORMATION: MTD 2103 polynucleotide Sequence

<400> SEQUENCE: 45
atgcacctgg cgctgccggt gctgctgctg gcg            33

<210> SEQ ID NO 46
<211> LENGTH: 42
<212> TYPE: DNA
<213> ORGANISM: Artificial Sequence
<220> FEATURE:
<223> OTHER INFORMATION: MTD 2159 polynucleotide Sequence

<400> SEQUENCE: 46
atgcacattg cgattgcggc gattccggcg attctggcgc tg            42

<210> SEQ ID NO 47
<211> LENGTH: 33
<212> TYPE: DNA
<213> ORGANISM: Artificial Sequence
<220> FEATURE:
<223> OTHER INFORMATION: MTD 2173 polynucleotide Sequence

<400> SEQUENCE: 47
atgcacgcgg tgattccgat tctggcggtg ccg            33

<210> SEQ ID NO 48
<211> LENGTH: 48
<212> TYPE: DNA
<213> ORGANISM: Artificial Sequence
<220> FEATURE:
<223> OTHER INFORMATION: MTD 2018m polynucleotide Sequence

<400> SEQUENCE: 48
atgcacccgg cggcgctggc ggcgctgccg gtggcggtgg tggcggtg            48

<210> SEQ ID NO 49
<211> LENGTH: 33
<212> TYPE: DNA
<213> ORGANISM: Artificial Sequence
<220> FEATURE:
<223> OTHER INFORMATION: MTD 2173A polynucleotide Sequence

<400> SEQUENCE: 49
atgcacccgg cggtgattcc gattctggcg gtg            33

<210> SEQ ID NO 50
<211> LENGTH: 48
<212> TYPE: DNA
<213> ORGANISM: Artificial Sequence
<220> FEATURE:
<223> OTHER INFORMATION: MTD 3018 polynucleotide sequence

<400> SEQUENCE: 50
atgaaggcgg cgctgattgg cgcggtgctg gcgccggtgg tggcggtg        48

<210> SEQ ID NO 51
<211> LENGTH: 30
<212> TYPE: DNA
<213> ORGANISM: Artificial Sequence
<220> FEATURE:
<223> OTHER INFORMATION: MTD 3067 polynucleotide Sequence

<400> SEQUENCE: 51
atgaaggcgg cggcgccggc ggtggcggcg                             30

<210> SEQ ID NO 52
<211> LENGTH: 33
<212> TYPE: DNA
<213> ORGANISM: Artificial Sequence
<220> FEATURE:
<223> OTHER INFORMATION: MTD 3103 polynucleotide Sequence

<400> SEQUENCE: 52
atgaagctgg cgctgccggt gctgctgctg gcg                         33

<210> SEQ ID NO 53
<211> LENGTH: 42
<212> TYPE: DNA
<213> ORGANISM: Artificial Sequence
<220> FEATURE:
<223> OTHER INFORMATION: MTD 3159 polynucleotide Sequence

<400> SEQUENCE: 53
atgaagattg cgattgcggc gattccggcg attctggcgc tg               42

<210> SEQ ID NO 54
<211> LENGTH: 33
<212> TYPE: DNA
<213> ORGANISM: Artificial Sequence
<220> FEATURE:
<223> OTHER INFORMATION: MTD 3173 polynucleotide Sequence

<400> SEQUENCE: 54
atgaaggcgg tgattccgat tctggcggtg ccg                         33

<210> SEQ ID NO 55
<211> LENGTH: 48
<212> TYPE: DNA
<213> ORGANISM: Artificial Sequence
<220> FEATURE:
<223> OTHER INFORMATION: MTD 3018m polynucleotide Sequence

<400> SEQUENCE: 55

```
atgaagccgg cggcgctggc ggcgctgccg gtggcggtgg tggcggtg          48
```

```
<210> SEQ ID NO 56
<211> LENGTH: 33
<212> TYPE: DNA
<213> ORGANISM: Artificial Sequence
<220> FEATURE:
<223> OTHER INFORMATION: MTD 3173A polynucleotide Sequence

<400> SEQUENCE: 56
```

```
atgaagccgg cggtgattcc gattctggcg gtg                          33
```

```
<210> SEQ ID NO 57
<211> LENGTH: 10
<212> TYPE: PRT
<213> ORGANISM: Artificial Sequence
<220> FEATURE:
<223> OTHER INFORMATION: 48th to 57th basic amino acids of the Tat
      protein

<400> SEQUENCE: 57
```

Gly Arg Lys Lys Arg Arg Gln Arg Arg Arg
 1               5                   10

```
<210> SEQ ID NO 58
<211> LENGTH: 16
<212> TYPE: PRT
<213> ORGANISM: Artificial Sequence
<220> FEATURE:
<223> OTHER INFORMATION: Antennapedia homeodomain-derived penetratin

<400> SEQUENCE: 58
```

Arg Gln Ile Lys Ile Tyr Phe Gln Asn Arg Arg Met Lys Trp Lys Lys
 1               5                   10                  15

```
<210> SEQ ID NO 59
<211> LENGTH: 12
<212> TYPE: PRT
<213> ORGANISM: Artificial Sequence
<220> FEATURE:
<223> OTHER INFORMATION: MTS derived from a signal peptide of a FGF

<400> SEQUENCE: 59
```

Ala Ala Val Leu Leu Pro Val Leu Leu Ala Ala Pro
 1               5                   10

```
<210> SEQ ID NO 60
<211> LENGTH: 10
<212> TYPE: PRT
<213> ORGANISM: Artificial Sequence
<220> FEATURE:
<223> OTHER INFORMATION: MTD-coumaric acid derivative
<220> FEATURE:
<221> NAME/KEY: MISC_FEATURE
<222> LOCATION: (1)..(1)
<223> OTHER INFORMATION: (4-Hydroxycinnamoyl)

<400> SEQUENCE: 60
```

Ala Ala Val Ala Pro Ala Ala Ala Arg Met
 1               5                   10

```
<210> SEQ ID NO 61
<211> LENGTH: 15
<212> TYPE: PRT
<213> ORGANISM: Artificial Sequence
<220> FEATURE:
<223> OTHER INFORMATION: modified MTD-acetyl pentapeptide
<220> FEATURE:
```

```
<221> NAME/KEY: MISC_FEATURE
<222> LOCATION: (11)..(11)
<223> OTHER INFORMATION: acetylated lysine

<400> SEQUENCE: 61

Met Arg Ala Ala Ala Pro Ala Val Ala Ala Lys Thr Thr Lys Ser
 1               5                  10                  15
```